US006454862B1

(12) United States Patent
Yoshida et al.

(10) Patent No.: US 6,454,862 B1
(45) Date of Patent: Sep. 24, 2002

(54) FINE-PARTICLE CLASSIFICATION APPARATUS AND FUNCTIONAL MATERIAL PRODUCTION APPARATUS

(75) Inventors: Takehito Yoshida, Machida; Toshiharu Makino, Kawasaki; Nobuyasu Suzuki, Kawasaki; Yuka Yamada, Kawasaki, all of (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/432,800

(22) Filed: Nov. 3, 1999

(30) Foreign Application Priority Data

Nov. 5, 1998 (JP) .......................................... 10-314297

(51) Int. Cl.[7] ............................................. C23C 14/00
(52) U.S. Cl. ................... 118/722; 118/726; 209/127.1; 209/128; 209/129; 209/130; 96/16; 73/28.02; 73/865.5; 204/298.26
(58) Field of Search ............................... 118/722, 726; 209/127.1, 128, 129, 130; 96/16; 73/28.02, 865.5; 204/298.26

(56) References Cited

U.S. PATENT DOCUMENTS

| | | | | |
|---|---|---|---|---|
| 4,574,004 A | * | 3/1986 | Schmidt-Orr | 55/4 |
| 4,987,007 A | * | 1/1991 | Wagal | 118/50.1 |
| 5,395,735 A | * | 3/1995 | Nagata | 430/270 |
| 5,431,714 A | * | 7/1995 | Burtscher | 95/97 |
| 5,622,567 A | * | 4/1997 | Kojima | 118/726 |
| 5,733,609 A | * | 3/1998 | Wang | 427/561 |
| 6,239,453 B1 | * | 5/2001 | Yamada | 257/79 |

FOREIGN PATENT DOCUMENTS

| | | |
|---|---|---|
| JP | 08-306485 | * 11/1996 |
| JP | 9-269288 | 10/1997 |
| JP | 9-275075 | 10/1997 |
| WO | WO97/49119 | * 12/1997 |

OTHER PUBLICATIONS

Chrisey, Pulsed Laser Deposition of Thin Films, John Wiley and Sons, New York, 1994, pp. 4 and 42–46.*
Zheng, Appl. Phys. Lett., vol. 63, pp. 1–3, 1993.*
English language abstract of JP 9–275075.
English language abstract of JP 9–269288.
T. Seto, et al., "Size Distribution Measurement of Nanometer–sized Aerosol Particles Using DMA Under Low–Pressure Conditions," in Journal Aerosol Science, vol. 28, pp. 193–206, 1997.
P.J. Ziemann, et al., "Particle Beam Mass Spectrometry of Submicron Particles Charged to Saturation in an Electron Beam," Journal Aerosol Science, vol. 26, No. 5, pp. 745–756, 1995.
C. Kanaoka, et al., Research Report in Journal of Powder Chemical Engineering Association, Vo. 21, No. 12, 1984, pp. 753–758.

* cited by examiner

*Primary Examiner*—Richard Bueker
(74) *Attorney, Agent, or Firm*—Greenblum & Bernstein, P.L.C.

(57) ABSTRACT

In the fine-particle classification apparatus of the present invention, a carrier gas velocity in a take-in section to introduce the aerosol to the fine-particle classification apparatus from the aerosol generation apparatus is increased so as to decrease the static pressure in the take-in section. It is thereby possible to decrease the static pressure in the take-in section than the total pressure in the aerosol generation apparatus. As a result, it is possible to introduce the aerosol inside the fine-particle classification apparatus with a total pressure equal to or higher than that in the aerosol generation apparatus from a fine particle generating area, i.e. aerosol generation apparatus with a pressure equal to or lower than that in the fine-particle classification apparatus.

16 Claims, 11 Drawing Sheets

FINE-PARTICLE CLASSIFICATION APPARATUS AND FUNCTIONAL MATERIAL PRODUCTION APPARATUS

BACKGROUND OF THE INVENTION

1. Field of the Invention

The present invention relates to a fine-particle classification apparatus for classifying fine particles in an aerosol in a gas phase, and more particularly, to a fine-particle classification apparatus for charging target fine particles in the aerosol and further applying an electrostatic field to the particles, thereby classifying the particles using a difference between each mobility which depends on the particle diameter.

2. Description of the Related Art

As a system for fine-particle classification apparatus for classifying fine particles in an aerosol, there have been a variety of types conventionally. The following describes about the Differential Mobility Analyzing (hereinafter referred to as DMA) which is the first conventional example for the fine-particle classification apparatus. In DMA, when fine particles in an aerosol are classified, target particles are first charged. The charged target fine particles are next applied an electrostatic field. The classification is performed using that the mobility of a particle in a medium gas is different depending on the particle size (diameter). The details for DMA are described, for example, in Journal of Aerosol Science, Vol.28, No.2, pp.193 to 206, 1997.

The following next describes the Particle Beam Mass Spectrometry (hereinafter referred to as PBMS) which is the second conventional example for the fine particle classification apparatus. In PBMS, target particles are focused into a beam with an ultra-sonic velocity in a process where enclosed fine particles are injected from a particle source to an ultra-high vacuum environment. The beam with the ultra-sonic velocity of fine particles is next charged in an electron beam. The charged target fine particles are then applied an electric field in the ultra-high vacuum environment, thereby performing a classification corresponding to a mass of a fine particle. The details of PBMS are described, for example, in Journal of Aerosol Science, Vol.26. No.5, pp.745 to 756, 1995.

In the first conventional example, it is necessary that an operation gas pressure in the DMA type classification apparatus be high, for which one of the reason is that the development thereof was started in the premise that an aerosol with an atmospheric pressure was sampled to classify. Therefore, it is considered that the operation gas pressure with more than a range of 50 to 100 Torr be necessary even in a recent reduced pressure DMA type classification apparatus.

The classification accuracy for the DMA type classification apparatus is determined by the degree of Brownian diffusion of the target fine particle in the aerosol. In detail, a great degree of Brownian diffusion means a great displacement by a fluctuation of the fine particle. When the Brownian diffusion of the fine particle is great, it is not possible to perform an accurate classification. Accordingly, when an inert gas with a low gas pressure and a small mass as a medium gas in the DMA type classification apparatus, the degree of Brownian diffusion becomes great, and the degree of classification accuracy in the DMA type classification apparatus deteriorates. Therefore, it is desired to use an inert gas with a high gas pressure and a great mass to some degree as the medium gas inside the DMA type classification apparatus.

On the other hand, it is necessary to lower a gas pressure inside an aerosol generation apparatus for generating an aerosol containing fine particles at a gas phase. In order to generate nm-sized fine particles, in particular, with a particle diameter of less than 10 nm to produce functional materials, it is desired to prepare inert background gases with a small mass as possible, and to make the gas pressure less than 50 Torr, inside the aerosol generation apparatus. It is because when inert background gases with a high gas pressure and a great mass are prepared inside the aerosol generation apparatus, generated fine particles are aggregated and grown to large sizes thereof.

The thus generated fine particles are classified, and the classified fine particles are deposited on a substrate, thereby producing the functional materials. In this case, since the process for depositing the fine particles on the substrate is performed after the classification process, it is necessary to flow the fine particles in the DMA type classification apparatus from the aerosol generating apparatus. It is effective to use a differential pressure introduction to flow the fine particles in the DMA type classification apparatus from the aerosol generation apparatus. Therefore, it is necessary to lower a pressure inside the DMA type classification apparatus than that inside the aerosol generation apparatus.

However, as described above, it is desired that the gas pressure inside the DMA type classification apparatus be high to improve the classification accuracy. There is thus a problem that it is difficult to improve the classification accuracy in the method of introducing the aerosol from the aerosol generation apparatus to the DMA classification apparatus using the pressure difference.

On the contrary, in the second conventional example, since the inside of the PBMS type classification apparatus is set to a high vacuum, the pressure inside the PBMS type classification apparatus is lower than that inside the aerosol generation apparatus.

However, in order to classify the fine particles with a diameter of several nm without lowering the yield in the PBMS type classification apparatus, aerodynamic lenses are needed to focus fine particles into a beam in the process that the fine particles are injected from a source. It is very difficult to design the aerodynamic lenses with a high yield and a low dispersion of the kinetic energy. Further, it is necessary that the electric grounding of walls of a vacuum chamber in the PBMS type classification apparatus be set at a level equal to or less than 0.1 volt (V) over the entire apparatus in order to keep a size of the PBMS type classification apparatus within a size range for practical use. There is thus another problem that the production of the PBMS type classification apparatus is very difficult.

SUMMARY OF THE INVENTION

An object of the present invention is to provide a fine-particle classification apparatus capable of introducing an aerosol inside the fine-particle classification apparatus with a total pressure equal to or higher than that inside the aerosol generation apparatus, and classifying fine particles from the introduced aerosol.

The main subject of the present invention is to increase a carrier gas velocity in a take-in section for introducing the aerosol to the fine-particle classification apparatus from the aerosol generation apparatus so as to decrease a static pressure in the take-in section, thereby introducing the aerosol inside the fine-particle classification apparatus with a total pressure equal to or higher than that in the aerosol generation apparatus from a fine particle generating area, i.e., aerosol generation apparatus with the total pressure equal to or lower than that in the fine-particle classification apparatus.

Further, it is preferable in the present invention that the take-in section made at a side of the fine-particle classification apparatus have a piping structure in which a specific carrier gas flows, and that a diameter of the introduction section be smaller than diameters of pipes connected to the front and back portion of the take-in section, whereby the carrier gas velocity is increased locally in the introduction section. As a result, it is possible to lower the static pressure in the introduction section effectively.

It is further desired in the present invention to introduce, as a carrier gas or sheath gas inside the fine-particle classification apparatus, a medium gas of which the kind is different from that of the medium gas used in the aerosol generation apparatus, in particular, the medium gas with a mass greater than that of the medium gas used in the aerosol generation apparatus.

It is thus possible to lower the static pressure in the introduction section further effectively. As a result, it is possible to introduce the aerosol to the fine particle classification apparatus further efficiently. Further, by the use of the medium gas with a great mass as the medium gas (carrier gas or sheath gas) inside the fine-particle classification apparatus, it is possible to suppress Brownian diffusion of target particles in the fine-particle classification apparatus, thereby making it possible to improve the classification accuracy in the fine-particle classification apparatus.

BRIEF DESCRIPTION OF THE DRAWINGS

The above and other objects and features of the invention will appear more fully hereinafter from a consideration of the following description taken in connection with the accompanying drawing wherein one example is illustrated by way of example, in which.

DETAILED DESCRIPTION OF THE PREFERRED EMBODIMENTS

First Embodiment

Figure 1:
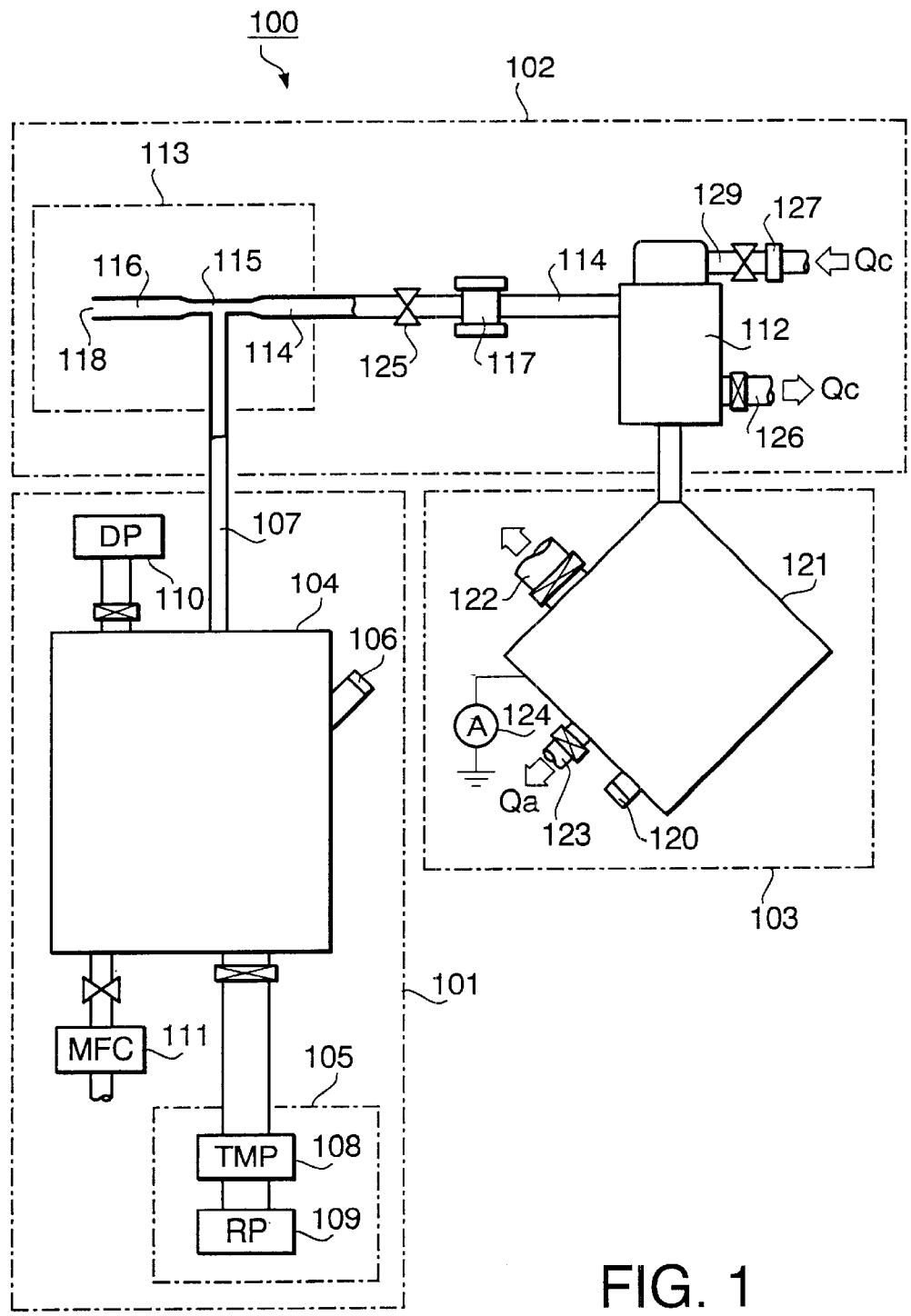
FIG. 1 is a diagram illustrating a configuration of a functional material production apparatus according to a first embodiment of the present invention.

A functional material production apparatus according to the first embodiment of the present invention is specifically explained using accompanying drawings. FIG. 1 illustrates a diagram of a configuration of the inside of the functional material production apparatus according to the first embodiment.

Functional material production apparatus 100 is provided with aerosol generation section 101 which generates an aerosol containing fine particles. Aerosol generation section 101 is connected with aerosol classification section 102 by first aerosol carrying pipe 107. Aerosol classification section 102 classifies the fine particles in the aerosol generated in aerosol generation section 101. Aerosol classification section 102 is connected with deposition section 103 with fine-particle deposition nozzle 119. Deposition section 103 deposits the fine particles classified aerosol classification section 102.

The next description explains aerosol generation section 101. Aerosol generation section 101 is provided with fine-particle generation chamber 104. Fine-particle generation chamber 104 functions as a chamber for actually generating the aerosol containing fine particles. Provided at the bottom of fine-particle generation chamber 104 is vacuum evacuation system 105 which reduces a pressure inside fine-particle generation chamber 104. Provided at a side wall of fine-particle generation chamber 104 is introduction window 106. By the use of introduction window 106, it is possible to introduce a pulse laser beam radiated from a light source toward a solid target which is not shown in the figure but provided inside fine-particle generation chamber 104. Provided at an upper portion in fine-particle generation chamber 104 is first aerosol carrying pipe 107. The aerosol ejected from the solid target is supplied to aerosol classification section 102 through first aerosol carrying pipe 107.

An end of first aerosol carrying pipe 107 is extended to a portion where the solid target is placed in fine-particle generation section chamber 104. Provided at a tip of first aerosol carrying pipe is an aerosol collection inlet which is not shown in the figure. The aerosol collection inlet collects the aerosol generated in fine-particle generation chamber 104.

As vacuum evacuation system 105, turbo molecular pump 108 is connected with fine-particle generation chamber 104. Turbo molecular pump 108 is connected with rotary pump 109.

Dry pump 110 is connected to an upper portion of fine-particle generation chamber 104. When an ambient inert gas is introduced inside fine-particle generation section 104, dry pump 110 differential-exhausts the gas, and sets the ambient inert gas pressure at a constant value (about several to 100 Torr). Fine-particle generation chamber 104 is further connected with mass flow controller 111. Mass flow controller 111 controls a flow rate of the ambient inert gas to be introduced inside fine-particle generation chamber 104.

In fine-particle generation chamber 104 with the configuration as described above, after the solid target is first placed, the pressure inside is reduced by vacuum evacuation system 105, and then the ambient inert gas is introduced. Next, dry pump 110 differential-exhausts the ambient inert gas, and sets the ambient inert gas pressure at a constant value (about several to 10.0 Torr). Under such a condition, the pulse laser beam radiated from the light source being present outside fine-particle generation chamber 104 is introduced into fine-particle generation chamber 104 through introduction window 106 to irradiate the solid target. By irradiating the solid target with the pulse laser, atoms, ions and clusters are ejected from a surface of the excited solid target. The ejected species are collided and aggregated together, and then grown to fine particles in the gas phase, while repeating collisions to each other and also with molecules (atoms) of the ambient gas, thus generating an aerosol. The generated aerosol is collected from the aerosol collection inlet of first aerosol carrying pipe 107, and transferred to aerosol classification section 102 through first aerosol carrying pipe 107.

The next description explains aerosol classification section 102. Aerosol classification section 102 has aerosol take-in apparatus 113 at a position connected with aerosol generation section 101. Aerosol take-in apparatus 113 introduces the aerosol generated in aerosol generation section 101 through aerosol carrying pipe. Aerosol classification section 102 further has fine-particle classification apparatus 112 at a position connected with aerosol take-in apparatus 113. Fine-particle classification apparatus 112 classifies the fine particles from the aerosol introduced from aerosol take-in apparatus 113. Aerosol take-in apparatus 113 uses a carrier gas with an adequate velocity to introduce the aerosol generated in aerosol generation section 101 into fine-particle classification apparatus 112 using a pressure difference.

Aerosol take-in apparatus 113 is connected with another end of first aerosol carrying pipe 107. In the middle of aerosol take-in apparatus 113, aerosol take-in section 115 is provided at a position connected with first aerosol carrying pipe 107. Aerosol take-in section 115 introduces the aerosol supplied from aerosol generation section 104. First aerosol carrying pipe 107 is connected to the middle portion of aerosol take-in section 115.

An end of aerosol take-in section 115 is connected with carrier gas piping 116. The other end of carrier gas pipe is provided with carrier gas introduction inlet 118 for supplying a carrier gas toward aerosol take-in section 115. The carrier gas has a function for carrying the aerosol introduced into aerosol take-in section 115 to fine-particle classification apparatus 112.

Another end of aerosol take-in section 115, which is the opposite end to carrier gas piping 116, is connected with second aerosol carrying pipe 114 for supplying the aerosol introduced into aerosol introduction section 115 to fine-particle classification apparatus 112. Aerosol take-in section 115, carrier gas piping 116 and second aerosol carrying pipe 114 are all structured in the form of pipes. The diameter of aerosol take-in section 115 is designed to be smaller than that of second aerosol carrying pipe 114 and that of carrier gas piping 116.

In other words, carrier gas piping 116 and aerosol take-in section 115 are provided to supply the carrier gas to fine-particle classification apparatus 112 without changing a flow direction of the carrier gas. First aerosol carrying pipe 107 is connected almost vertically to the direction where carrier gas piping 116 and aerosol take-in section 115 are connected. First aerosol carrying pipe 107 is provided to supply the aerosol generated in aerosol generation section 101 to a flow of the carrier gas flowing in carrier gas piping 116 and aerosol take-in section 115. The diameter of an area where the aerosol joins the flow of the carrier gas in aerosol take-in section 115 is smaller than that of carrier gas piping 116 which is present at an upper stream portion than the portion where the aerosol joins the stream of the carrier gas.

Second aerosol carrying pipe 114 is provided with valve 125 being present between aerosol take-in apparatus 113 and fine-particle classification apparatus 112. Ionization chamber 117 for ionizing the aerosol is provided between aerosol take-in apparatus 113 and fine-particle classification apparatus 112, and at a side which is closer to fine-particle classification apparatus 112 than valve 125. Inside ionization chamber 117, americium (Am) that is one of radioactive isotopes is placed to charge the aerosol passing therein. Further in ionization chamber 117, the fine particles are charged with a high-density ultraviolet light source such as an ArF excimer laser with a wavelength of 193 nm, thereby making it possible to charge the fine particles with a monopole with high efficiency. It is thereby possible to improve the yield of classified particles. In addition, although the ArF excimer laser is used in this embodiment, it may be possible to use an excimer lamp and Deep Ultra Violet (DUV) lamp as an ultraviolet light source.

Fine-particle classification apparatus 112 is next explained. Fine-particle classification apparatus 112 is composed of a double-cylinder type DMA fine-particle classification apparatus. Fine-particle classification apparatus 112 is provided with mass flow controller 127. Mass flow controller 127 controls a flow rate of the sheath gas which is indispensable when the fine particles are classified from the aerosol and introduced inside fine-particle classification apparatus 112.

Mass flow controller 127 is connected with a sheath gas carrying pipe for carrying the sheath gas inside fine-particle classification apparatus 112. Provided at a right wall of fine-particle classification apparatus 112 is sheath gas differential-exhaustion system 126 for exhausting the sheath gas inside fine-particle classification apparatus 112. Sheath gas differential-exhaustion system 126 is primarily composed of a rotary pump connected to a large-sized mechanical booster pump. Provided at a bottom of fine-particle classification apparatus 112 is fine-particle deposition nozzle 119 for carrying the carrier gas with a constant mass flow rate $Q_a$ (for example, 11/min. at standard conditions) containing the fine particles classified to have a uniform diameter in fine-particle classification apparatus 112, and injecting such a carrier gas inside deposition section 103.

aerosol classification section 102 with the configuration as described above, the aerosol supplied to aerosol classification section 102 through first aerosol carrying pipe 107 is introduced to aerosol take-in section 115 in aerosol take-in apparatus 113. The introduced aerosol is supplied to fine-particle classification apparatus 112 through second aerosol carrying pipe 114 by the carrier gas introduced from carrier gas introduction inlet 118. The aerosol is ionized in ionization chamber 117 on the way to be supplied to fine-particle classification apparatus 112. The fine particles contained in the aerosol supplied to fine-particle classification apparatus 112 are classified to particles with a uniform diameter, and carried to deposition section 103 with the carrier gas with the constant mass flow rate $Q_a$.

Deposition section 103 is next explained. Deposition section 103 is provided with deposition chamber 121 for depositing the classified fine particles. The upper portion of deposition chamber 121 is connected to fine-particle classification apparatus 112 through fine-particle deposition nozzle 119. Provided at a left side surface of deposition chamber 121 is laser beam introduction window 120 to introduce an excimer laser beam inside deposition chamber 121. By the use of the laser beam introduction window, it is possible to introduce the excimer laser beam to a transparent medium target, which is not shown in the figure, but prepared inside deposition chamber 121. Provided at a left side portion of deposition chamber 121 is ultra-high vacuum evacuation system 122 for evacuating deposition chamber 121 to be ultra-high vacuum of less than $1 \times 10^{-7}$ Torr prior to the production of an optical functional element. Further provided at the left side portion of deposition chamber 121 is carrier gas differential-exhaustion system 123 which performs the differential-exhaustion of the carrier gas to hold the pressure inside deposition chamber 121 at a constant pressure P2 (for example, 2.0 Torr).

Deposition chamber 121 is provided with minute-ampere meter 124 which measures as a current a transfer of charged fine particles (electron transfer) carried out when the classified charged fine particles are deposited on a deposition substrate in deposition chamber 121.

The carrier gas is carried inside deposition section 103 configured as described above. The carrier gas has a constant mass flow rate $Qa$ and contains the fine particles with a uniform diameter classified in fine-particle classification apparatus 112. In deposition chamber 121, the classified fine particles supplied from fine-particle classification apparatus 112 are deposited, thereby producing a functional material.

Figure 2:
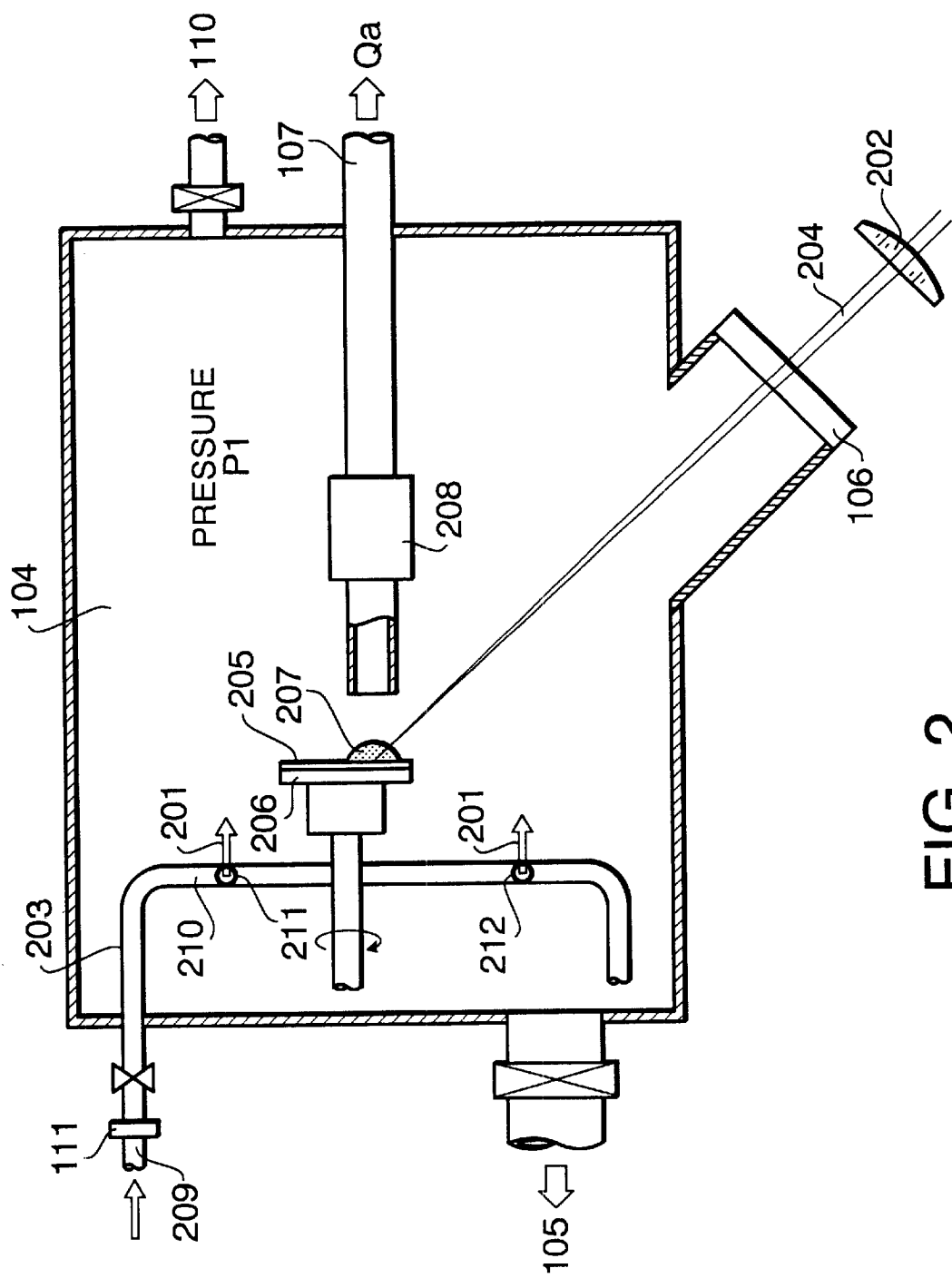
FIG. 2 is a diagram illustrating a configuration of a fine-particle generation chamber in the functional material production apparatus illustrated FIG. in 1.

Fine-particle generation chamber 104 according to the first embodiment is next explained specifically using FIG. 2. FIG. 2 is a configuration diagram of the fine-particle generation chamber according to the first embodiment.

Gas introduction system 209 is provided at a left side wall of fine-particle generation chamber 104. Mass flow controller 111 is provided at an end of gas introduction system 209. Mass flow controller 111 is set to introduce an ambient inert gas 201 inside fine-particle generation chamber 104 with the constant mass flow rate $Qa$. Mass flow controller 111 is connected to ambient inert gas introduction pipe 203 which is extended to a direction for the inside of fine-particle generation chamber 104 almost vertically to mass flow controller 111. Ambient inert gas introduction pipe 203 is connected to ambient inert gas injection pipe 210 which is bent almost vertically at a portion closed to the side surface inside fine-particle generation chamber 104. Two ambient inert gas injection outlets 211 and 212 are formed on ambient inert gas injection pipe 210. Ambient inert gas injection outlets 211 and 212 are provided with semiconductor target 205, which is a solid target described later, between with almost equal distances therefrom. Thus, the ambient inert gas forms symmetry flows to semiconductor target 205.

Introduction window 106 is provided at a side surface next to the surface with gas introduction system 209 in fine-particle generation chamber 104. Introduction window 106 is used to introduce pulse laser beam 204 to the semiconductor target inside fine-particle generation chamber 104. Converging lens 202 is provided outside fine-particle generation chamber 104 near introduction window 106 to converge pulse laser beam 204. Pulse laser beam 204 converged by converging lens 202 is introduced into fine-particle generation chamber 104 through introduction window 106.

Semiconductor target 205 is placed at a position which is almost center of the inside of fine-particle generation chamber 104 and a little close to gas introduction system 209. Semiconductor target 205 is a solid target which is a base material to generate fine particles.

Semiconductor target 205 is fixed to a target holder 206 which has a rotation structure. Target holder 206 is placed at a position so that semiconductor target 205 is irradiated by pulse laser beam 204 which is introduced inside fine-particle generation chamber 104. Semiconductor target 205 is excited by pulse laser beam 204 (for example, the second harmonic wave of Nd-YAG laser with a wavelength of 532 nm) introduced into fine-particle generation. chamber 104. Excited semiconductor target 205 forms ablation plume 207. Species, which are ejected from a surface of semiconductor target 205 and grown to fine particles in the neighborhood outside ablation plume 207, are introduced into fine-particle take-in pipe 208.

Fine-particle take-in pipe 208 is placed near ablation plume 207 toward a growing direction of ablation plume 207, so that the fine particles in the neighborhood of ablation plume 207 is easily introduced into fine-particle take-in pipe 208. Fine-particle take-in pipe 208 is connected to first aerosol carrying pipe 107. The fine particles introduced into fine-particle take-in pipe 208 are supplied to first aerosol carrying pipe 107, and then supplied to aerosol take-in apparatus 113.

Figure 3:
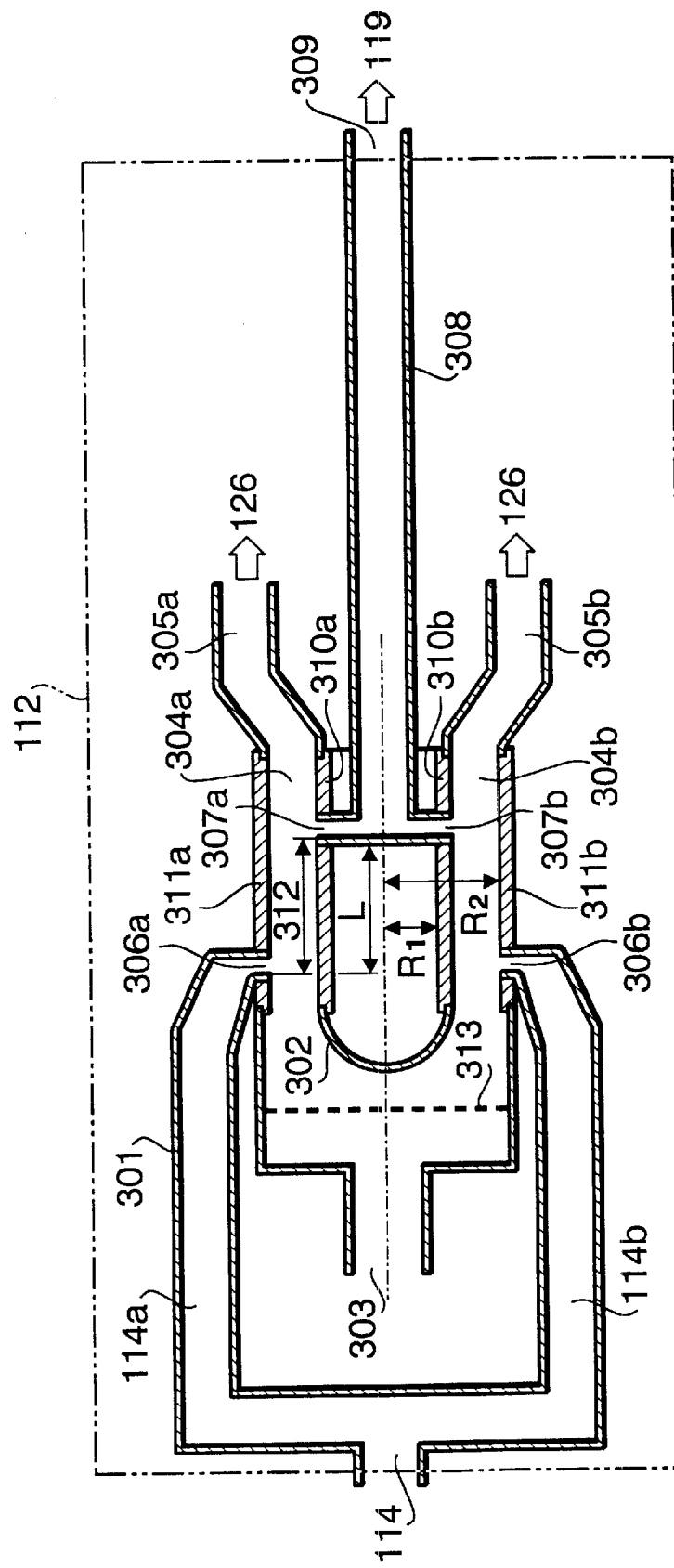
FIG. 3 is a diagram illustrating a configuration of a fine-particle classification apparatus in the functional material production apparatus illustrated FIG. in 1.

Fine-particle classification apparatus 112 according to the first embodiment is next explained using FIG. 3. FIG. 3 is a configuration diagram of the fine-particle classification apparatus according to the first embodiment.

Fine-particle classification apparatus 112 adopts a double-cylinder type DMA fine-particle classification method. Fine-particle classification apparatus 112 is provided with outer cylinder 301 having the cylinder-like form as a main body of the apparatus. Inner cylinder 302 is provided inside outer cylinder 301. The central axis of outer cylinder 301 and that of inner cylinder 302 are placed at almost the same position. In other words, outer cylinder 301 and inner cylinder 302 have the common central axis. Second aerosol carrying pipe 114 previously described is connected to the left portion of fine-particle classification apparatus 112.

Outer cylinder 301 has the cylinder-like form of which an upstream portion (rear end portion: hereinafter, a front portion in the direction of the flow of the aerosol is referred to as a top or front portion, and an inverse portion is referred to as a rear portion) and a top end are opened. Sheath gas introduction inlet 303 is provided at the upstream portion. The diameter of sheath gas introduction inlet 303 becomes smaller from outer cylinder 301 as a base, making a step-like form. Filter mesh 313 is provided inside sheath gas introduction inlet 303. The sheath gas is flown to a space between outer cylinder 301 and inner cylinder 302 (which is classification region 312 in the narrow sense). At this point, by the use of filter mesh 313, the sheath gas can be laminar flow effectively in classification region 312 inside fine-particle classification apparatus 112.

Passes 304a and 304b are formed inside outer cylinder 301 in an intermediate portion in a longitudinal direction thereof. Passes 304a and 304ba are composed of spaces formed between outer cylinder 301 and inner cylinder 302. Sheath gas outlets 305a and 305b are respectively provided at the top portions of passes 304a and 305b. Aerosol injection slits 306a and 306b are provided in the form of circular rings at a side surface in an intermediate portion of outer cylinder 301 in the longitudinal direction thereof. Each of aerosol injection slits 306a and 306b is composed of a fine space linking between the outside and inside of outer cylinder 301.

Inner cylinder 302 is composed of a cylinder-like body with a diameter smaller than that of outer cylinder 301. The upstream portion of inner cylinder 302 is closed. On the other hand, the top end portion of inner cylinder 302 has an opened cap structure. Further, aerosol take-in slits 307a and 307b are formed in the form of circular rings at a side surface close to the top portion in the inner cylinder 302. Aerosol take-in slits 307a and 307b are respectively composed of fine spaces linking between the inside of inner cylinder 302, and passes 304a and 304b.

The top end portion of inner cylinder 302 is connected to aerosol extraction pipe 308 being extended from positions of aerosol take-in slits 307a and 307b to the top end portion. Formed at the top end portion of aerosol extraction pipe 308 is aerosol extraction outlet 309 from which the classified aerosol is extracted.

Second aerosol carrying pipe 114 is branched to a plurality of branch pipes 114a and 114b (two FIG. in 1) in fine-particle classification apparatus 112. Branch pipes 114a and 114b are branched in the symmetry forms to the common axis of double-cylinder structure of fine-particle classification apparatus 112. The top ends of branch pipes 114a and 114b are respectively connected to aerosol injection slits 306a and 306b, which are formed at a side surface of outer cylinder 301, from the outside of outer cylinder 301. Further, sheath gas exhaustion outlets 305a and 305b are connected to fine-particle classification apparatus 112 in the symmetry forms to the common axis of double-cylinder structure in the similar manner with second aerosol carrying pipe 114.

Cathode high-voltage electrodes 310a and 310b are attached in classification region 312 on an outer wall of inner cylinder 302. Grounding electrodes 311a and 311b are attached in classification region 312 on an inner wall of outer cylinder 301. A radial electrostatic field is formed around the common central axis by cathode high-voltage electrodes 310a and 310b, and grounding electrodes 311a and 311b.

Figure 4:
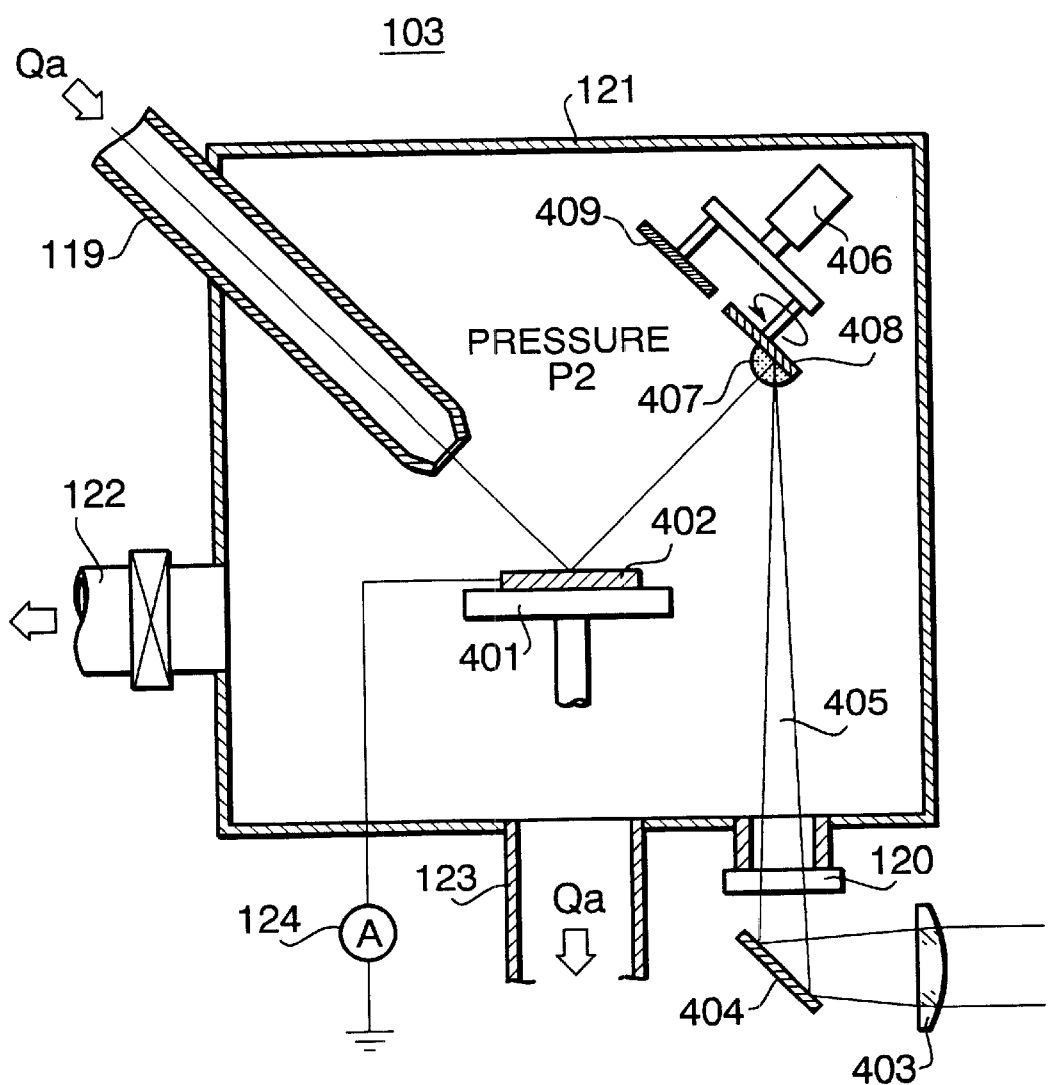
FIG. 4 is a diagram illustrating a configuration of a deposition chamber in the functional material production apparatus illustrated FIG. in 1.

A configuration of deposition section 103 is next explained specifically using FIG. 4. FIG. 4 is a configuration diagram of the deposition chamber according to the first embodiment.

Deposition section 103 is provided with deposition chamber 121. Fine-particle deposition nozzle 119 is provided at an upper portion on a side surface of deposition chamber 121. Fine-particle deposition nozzle 119 injects the carrier gas inside deposition chamber 121. The carrier gas has the constant mass flow rate Qa and contains the fine particles with a uniform diameter classified in fine-particle classification apparatus 112.

Laser beam introduction window 120 is provided at a position, which is symmetrical to fine-particle deposition nozzle 119 around a center of deposition chamber 121, in deposition chamber 121 to introduce excimer laser beam 405. Mirror 404 is provided near laser beam introduction window 120 outside deposition chamber 121 to change a running direction of excimer laser beam 405 by 90 degrees. Converging lens 403 is provided near mirror 404 to converge excimer laser beam 405.

Excimer laser beam 405 converged by converging lens 403, of which the direction is changed by 90 degrees with mirror 404, is introduced inside deposition chamber 121 through laser beam introduction window 120. Excimer laser beam 405 introduced inside deposition chamber 121 reaches transparent medium target 408.

Transparent medium target 408 is fixed to a target drive exchange mechanism 406 which carries out the drive and exchange of the target. Target drive exchange mechanism 406 is placed at a position arranged so that introduced excimer laser beam 405 irradiates transparent medium target 408. Specifically, target drive exchange mechanism 406 is provided near an upper portion on a side surface on the opposite side of the other side surface, on which fine-particle deposition nozzle 119 is provided, in deposition chamber 121. Transparent electrode material target 409, which is another transparent medium target, is also fixed to target drive exchange mechanism 406.

Transparent medium target 408 is excited by excimer laser beam 405 and forms ablation plume 407. Transparent medium target 408 and transparent electrode material target 409 are placed in such a manner that a growing direction of ablation plume 407 goes toward deposition substrate 402.

Deposition substrate 402, on which fine particles, transparent media and transparent electrodes are deposited, is placed at almost the center of deposition chamber 121. Deposition substrate 402 is fixed to deposition substrate holder 401.

Further, ultra-high vacuum evacuation system 122 is provided at a side portion at which fine-particle deposition nozzle 119 is provided. Ultra-high vacuum evacuation system 122 evacuates deposition chamber 121 to be ultra-high vacuum of less than $1 \times 10^{-7}$ Torr prior to the production of optical functional element. Carrier gas differential-exhaustion system 123 is provided at another side portion under deposition substrate 402 in deposition chamber 121. Carrier gas differential-exhaustion system 123 performs the differential exhaustion of the carrier gas to hold the pressure inside deposition chamber 121 at a constant pressure P2 (for example, 2.0 Torr).

Minute-ampere meter 124 is provided at a bottom of deposition chamber 121, and measures a transfer of charged particles carried out when the classified charged fine particles are deposited on deposition substrate 402 in deposition chamber 121. Minute-ampere meter 124 electrically detects the fine particles subjected to the classification to have a uniform diameter in fine-particle classification. Minute-ampere meter 124 also measures a diameter of classified fine particle and a concentration distribution thereof. Specifically, minute-ampere meter 124 measures such a transfer of fine particles as a current.

Operations in the functional material production apparatus according to the first embodiment are next explained specifically using FIG. 1 to FIG. 5.

The generation method of nm-sized fine particles in the first embodiment is first explained. In fine-particle generation chamber 104, semiconductor target 205 with high purity semiconductor such as silicon (Si) and germanium (Ge) is irradiated with converged pulse laser beam 204, whereby ions, atoms and clusters are ablated from a surface of semiconductor target 205. In fine-particle generation chamber 104, such ablated ions, atoms and clusters are condensed in a physical vapor phase in which inert gases such as helium (He) are filled, thereby generating fine-particles.

At this point, the size distribution of the generated fine particles varies depending on species of target materials, pulse laser irradiation conditions such as a wavelength, pulse width and energy density, inert gas pressure, and a distance and direction from the target.

What provides the most effect on the particle size distribution is the pressure of an inert gas. In the case where Si is used as a semiconductor solid material, and He is used as an inert gas, so-called nm-sized fine particles with diameters of several nm to several tens nm equal to or less than 50 nm are formed when the gas pressure almost ranges from 3 to 20 Torr.

Fine-particle generation chamber 104 is composed of SUS 304 alloy subjected to electrolytic polishing to be correspondent to ultra-high vacuum conditions. It is because nm-sized fine particles with a large number of surface exposed atoms (for example, in fine particles with a diameter of 5 nm, 40% of atoms are surface exposed atoms) are very sensitive to oxidation and impurity contamination. Further, used as each valve and flange connected to fine-particle generation chamber 104 is an ultra-high vacuum correspondent product capable of being baked at 200° C.

Further, the generation method of nm-sized fine particles according to the first embodiment is specifically explained. First, prior to the nm-sized fine-particle generation process, valve 125 illustrated in FIG. 1 is closed to eliminate the effects of damage and contamination. Next, fine-particle generation chamber 104 is evacuated using turbo molecular pump 108 as a main pump and rotary pump 22 as a backing pump. Thus, as the degree of achieved vacuum inside fine-particle generation chamber 104, the order of $10^{-10}$ Torr is achieved. After the inside of fine-particle generation chamber 104 is evacuated to the ultra-high vacuum, vacuum evacuation system 105 is closed.

At the same time as the aforementioned evacuation, fine-particle classification apparatus 112 and deposition chamber 121 are both evacuated to ultra-high vacuum of less than $1\times10^{-7}$ Torr with ultra-high vacuum evacuation system 122 composed of mainly turbo molecular pump. After fine-particle classification apparatus 112 and deposition chamber 121 are both evacuated, ultra-high vacuum evacuation system 122 is closed.

Next, when nm-sized fine particles are generated, He gas with high purity for semiconductor process (the purity thereof is more than 99.9999%) is introduced inside fine-particle generation chamber 104 with a constant flow rate of 200 sccm through mass flow controller 111. Used as mass flow controller 111 and gas introduction system 209 for the He gas with high purity for semiconductor process are high-purity correspondent products with EP grade. In this case, the inside of fine-particle generation chamber 104 is differential-exhausted with dry pump 110 without using turbo molecular pump 108, so that the pressure inside fine-particle generation chamber 104 is held at a constant He background gas pressure of 10.0 Torr.

In the reduced pressure He background gases as described above, semiconductor target 205 is fixed to target holder 206 in fine-particle generation chamber 104, and rotates with an angle velocity of 8 rpm (rotations/min). The pulse laser beam, which is introduced through laser beam introduction window 106 made of quarts, is converged and irradiated on semiconductor target 205, whereby the ablation occurs on the surface of semiconductor target 205.

Used as semiconductor target 205 is a high-purity Si single crystalline substrate (crystal orientation: (001); specific resistance: 10 Ω·cm). As pulse laser beam 204 to be converged and irradiated, the second harmonic wave of Q-switch Nd:YAG laser (wavelength: 532 nm; pulse energy: 10 mJ; pulse width: 40 ns; repetition rate: 10 Hz) is used, and converged and irradiated so that the energy density thereof becomes 10 J/cm² on the surface of semiconductor target 205.

The surface of semiconductor target 205 is excited by converged pulse laser beam 204. The ablation reaction is thereby generated on semiconductor target 205, whereby spontaneous oxide films formed on the surface semiconductor target 205 and impurities adhered thereon such as metal and/or carbon compounds are completely removed. Thereafter, differential-exhaustion system is closed. At this point, the oscillation of pulse laser beam 204 is stopped.

As described above, the natural oxide films formed on the surface of semiconductor target 205 are completely removed. It is thus possible to eliminate the effects of oxide films that are impurities for semiconductor fine particles and metal and carbon compounds adhered on the surface of semiconductor target 205, which have the possibility of contaminating to the semiconductor fine particles.

Next, valve 125 illustrated in FIG. 1 is opened, and the carrier gas is introduced to fine-particle classification chamber 112 and deposition chamber 121 with the constant mass flow rate Qa. At the same time, the sheath gas is introduced to fine-particle classification apparatus 112 with the mass flow rate $Q_c$ (5 l/min. at standard conditions) using the mass flow controller 127.

At this point, carrier gas differential-exhaustion system 123 in FIG. 1 is opened, and the carrier gas is exhausted with the constant mass flow rate Qa to hold the pressure inside deposition chamber 121 the a constant pressure P2 (for example, 2.0 Torr). At the same time as the aforementioned operation, sheath gas differential-exhaustion system 126 in FIG. 1 is opened, and the sheath is exhausted with the constant mass flow rate $Q_c$. At this point, the pressure inside fine-particle generation chamber 104 and the pressure inside deposition chamber 121 are respectively held at the constant pressure P1 (for example, 5.0 Torr) and the constant pressure P2.

Si species such ions, atoms and clusters ablated (ejected) from the surface of semiconductor target 205 repeat collisions with atoms of the ambient He gas, and thus dissipate the kinetic energy of initial ejection to the ambient He gas, facilitating collision of Si species. As a result, the aggregation of ablated (ejected) Si species in the physical vapor phase, i.e., the generation of nm-sized fine particles is carried out.

At this time, the size distribution of the generated nm-sized fine particles varies depending on species of target material, pulse laser irradiation conditions such as a wavelength, pulse width, and energy density, a distance and direction from the target, and ambient inert gas pressure.

As described previously, what provides the most effect on the particle size distribution is the pressure of ambient inert gas. When the ambient inert gas pressure is less than a threshold, the generation of nm-sized fine particles in the gas phase is rapidly suppressed. Then, the most part of ejected Si species is condensed on the deposition substrate as an amorphous Si film.

The threshold is in a range of about 3 to 5 Torr in the case where Si and He are used as materials, and a Q-switch laser with a pulse width of several to several tens ns is used as a laser. When the ambient inert gas pressure exceeds this threshold and becomes excessively high, the aggregation of nm-sized fine particles rapidly occurs. As a result, fine particles with apparent diameters of more than 20 nm are generated. Further, the particles with apparent diameters of more than 20 nm are aggregated to form particles like grape bunches, and a large number of such particles are observed. It is because the confinement effect (confinement effect of plume) of ejected Si species by ambient He gas becomes remarkable, whereby the spatial density of ejected Si species are excessively increased.

Therefore, in the first embodiment, 10.0 Torr is set as the ambient He gas pressure as a low value as possible for causing the generation of nm-sized fine particles. Further, there is a tendency that the growth of fine particles is facilitated as the distance from the surface of semiconductor target 205 becomes longer. Accordingly, in the first embodiment, the aerosol collection inlet of fine-particle take-in pipe 208 is placed at a position with a height of 2.0 cm vertically above the surface of semiconductor target 205.

Thus, the nm-sized fine particles generated in the gas phase are extracted as an aerosol with the ambient He gas. As a result, the kinetic energies of the nm-sized fine particles generated in the gas phase are dissipated and stayed in the gas phase, whereby the generation of large-sized particles caused by unnecessary aggregation is suppressed. The aerosol containing the collected Si nm-sized fine particles with He gas as the medium gas is flown to aerosol take-in section 115 in aerosol classification section 102 through first aerosol carrying pipe 107.

In the first embodiment, the total pressure of aerosol take-in section 113 configured at the side of aerosol classification section 102 is set at a value equal to or more than the total pressure of aerosol generation section 101.

It is because the classification accuracy in fine-particle classification apparatus 112 is determined by the degree of Brownian diffusion of target fine particles in the aerosol. Specifically, when an inert gas with a low gas pressure and a low mass is used as the medium gas inside fine-particle classification apparatus 112, the Brownian diffusion of the target particles in the aerosol becomes prominent, resulting in a tendency that the classification accuracy in DMA deteriorates. Therefore, it is desired that an inert gas with a high gas pressure and a large mass to some degree be used as the medium gas inside fine-particle classification apparatus 112. For this reason, it is necessary to make the total pressure inside fine-particle classification apparatus 112 high. Specifically, it is considered that as the total pressure inside fine-particle classification apparatus 112, the operation pressure more than 50 to 100 Torr be necessary. Further, as the total pressure inside fine-particle classification apparatus 112 is increased, that of aerosol take-in section 113 is also increased.

On the contrary, the pressure inside aerosol generation chamber is 10 Torr.

Generally, in the case where a fluid collides with a substance, the fluid flows along the substance after colliding with the substance. For example, when a gas is collided with a one end of the substance, the gas first collides with a surface of the substance which is vertical to the flow of the gas, and then flows along the surface of the substance parallel to the flow of the gas. In this case, the total pressure is applied to the surface of the substance which is vertical to the flow of the gas (a pressure applied to the surface of the substance which is vertical to the flow of the gas in the direction parallel to the flow of the gas), and the static pressure is applied to the surface of the substance which is parallel to the flow of the gas (a pressure applied to the surface of the substance which is parallel to the flow of the gas in the direction vertical to the flow of the gas). The total pressure is the sum of the static pressure and the dynamic pressure related to the gas density and gas velocity.

Figure 5:
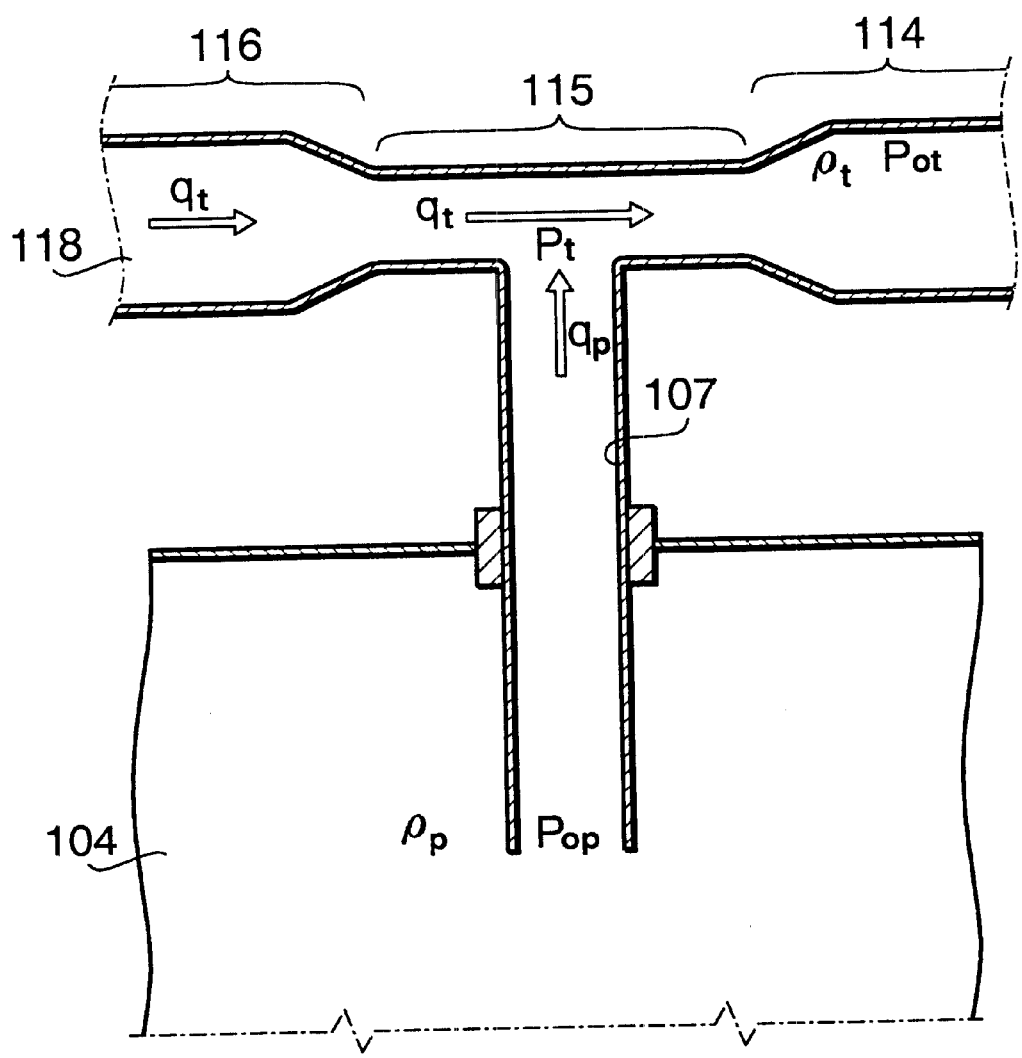
FIG. 5 is a diagram illustrating a configuration of an aerosol take-in section in the functional material production apparatus illustrated FIG. in 1.

As illustrated in FIG. 5, the substantial gas velocity inside fine-particle generation chamber 104 can be neglected. Further, there is a laminar flow with a gas velocity $q_t$ inside aerosol take-in section 115. Generally, there is a relationship between static pressure P, total pressure $P_o$, density ρ, and gas velocity q of the medium gas expressed with the following equation (1) from Bernoulli's theorem.

$$P + \frac{\rho q^2}{2} = P_0 \quad (1)$$

Hereinafter, affix "p" denotes the inside of fine-particle generation chamber 104, and affix "t" denotes the inside of aerosol take-in section 115. By adding the analysis of kinetic theory of gas molecules to the equation (1), the square of gas velocity $q_p$ which is an influx gas velocity to aerosol take-in section 115 from first aerosol carrying pipe 107 can be expressed with the following equation (2).

$$q_p^2 = \frac{2\gamma}{\gamma-1} \frac{P_{op}}{\rho_t} \left\{ 1 - \left( \frac{P_{ot} - \frac{\rho_t q_t^2}{2}}{P_{op}} \right)^{(\gamma-1)/\gamma} \right\} \quad (2)$$

Herein, γ is a ratio of specific heat of the medium gas and determined by a structure of gas molecule. γ of inert gases (single atom gases) such as Ar (argon) and He is 1.667 not depending on the kinds of gases.

As can be seen from the above equation (1), the static pressure is decreased by increasing the gas velocity. Further, when the static pressure is constant, the total pressure is increased by increasing the gas velocity.

The inventors of the present invention paid attention to this principle, and found out that it is possible to supply an aerosol from aerosol generation section 101 to aerosol classification section 102 inside which the pressure is equal to or higher than that inside aerosol generation section 101, by applying the principle to a structure of first aerosol carrying pipe 107 through which the aerosol is passed while being carried from aerosol generation section 101 to aerosol classification section 102.

This embodiment adopts a structure illustrated in FIG. 5 to apply the above-mentioned principle to first aerosol carrying pipe 107. In other words, aerosol take-in section 115, with a longitudinal direction which is vertical to a longitudinal direction of first aerosol carrying pipe 107, is connected to first aerosol carrying pipe 107. By applying such a configuration, it is possible to express an effective pressure inside aerosol take-in section 115 as the static pressure ($P_t$) and the effective pressure inside first aerosol carrying pipe 107 as the total pressure ($P_{op}$) when a transfer of a gas from first aerosol carrying pipe 107 to aerosol take-in section 115 is considered. Further, the gas velocity ($q_t$) of the carrier gas towards second aerosol carrying pipe 114 from carrier gas piping 116 corresponds to the gas velocity.

Thus, in the structure illustrated in FIG. 5, it is possible to substantially neglect the dynamic pressure inside first aerosol carrying pipe 107. On the basis of the equation (2), it is possible to decrease the static pressure ($P_t$) in the entrance of aerosol take-in section 115 by increasing the gas velocity ($q_t$) of the carrier gas. A decrease of the static pressure ($P_t$) in the entrance of aerosol take-in section 115 corresponds to that the effective pressure in the entrance of aerosol take-in section 115 is lower than the effective pressure ($P_{op}$) inside first aerosol carrying pipe 107, thereby enabling the differential pressure introduction. As a result, it is possible to supply the aerosol to aerosol classification section 102 from aerosol generation section 101. According to the principle previously described, since the gas velocity of the carrier gas can be increased further by decreasing the diameter of aerosol take-in section 115, it is possible to improve the efficiency of supplying the aerosol to aerosol classification section 102.

The principle described above originates in fluid dynamics. Therefore, when a gas with a reduced pressure is an object, it is necessary that the gas be in a viscous flow state. Accordingly, it is desired that the carrier gas be in the viscous flow state. Herein, the viscous flow state means a state where the mean free path λ of an atom composing the gas is extremely smaller than a parameter L representing a size of a flow pass (in this case, the diameter of aerosol take-in section 115) (λ<<L). In addition, gases with a large diameter of an atom /molecule (corresponding to a larger mass) tend to be in the viscous flow state since the mean free path thereof is small.

Specifically, the first embodiment adopts Ar with the total pressure of 25 Torr as the carrier gas, and further adopts He with the total pressure of 10 Torr as the aerosol medium gas for the fine-particle generation chamber side 104.

In this setting, when the gas velocity $q_t$ in aerosol take-in section 115 reaches 260 m/s, it is possible to flow the aerosol from first aerosol carrying pipe 107 to aerosol take-in section 115. In addition, the gas velocity $q_t$ in aerosol take-in section 115 has an upper limit. The upper limit value of the gas velocity is 336 m/s. Further, the influx gas velocity $q_p$ from first aerosol carrying pipe 107 to aerosol take-in section 115 also has the upper limit. The upper limit value of the influx gas velocity is 1680 m/s. The limit values of two kinds of gas velocities described above are determined by only the kind of gas (molecular weight and molecular structure) and temperature not without depending on the pressure setting. To be exact, this upper limit value of the gas velocity is the sound velocity.

Further, according to the equation (2), the static pressure $P_t$ is decreased by increasing the gas velocity $q_t$ in aerosol take-in section 115 particularly. It is thereby clarified that the introduction of the aerosol to aerosol take-in section 115 can be facilitated effectively. Further, it is possible to derive the effect on the gas velocity $q_t$ provided by each of other setting parameters such as $\rho_t$, $P_{ot}$, $\rho_p$ and $P_{op}$. The results are summarized in Table 1.

TABLE 1

| CARRIER GAS VELOCITY $q_t$ | $q_t^2$ |
|---|---|
| CARRIER GAS DENSITY $\rho_t$ | $\rho_t$ |
| TOTAL PRESSURE OF CARRIER GAS $p_{Ot}$ | $-P_{Ot}$ |
| AEROSOL MEDIUM GAS DENSITY $\rho_p$ | $\rho_p^{-1}$ |
| TOTAL PRESSURE OF AEROSOL MEDIUM GAS $p_{Op}$ | $P_{Op}$ |

In the first embodiment, the flow rate of Ar as the carrier gas is set at 2.0l/min (standard condition). In introducing the aerosol, a large amount of the flow rate is advantageous as described previously. However, as described later, the excessively increased flow rate introduces a high ratio to the sheath gas, thereby lowering the classification resolution. It is set to achieve the flow rate (2.0l/min) with 80% of the upper limit velocity 336 m/s for the gas velocity $q_t$ previously described. In this setting, it is derived that the diameter of aerosol take-in section 115 should be 2.5 mm. As carrier gas piping 116, ¼ inch pipes with an inner diameter of 4.3 mm are used from the availability of EP pipes with high cleanness and the necessity to ensure conductance over the entire piping. Therefore, aerosol take-in section 115 adopts a necking structure as illustrated in FIG. 5. Herein, the gas velocity $q_t$ of the carrier gas in aerosol take-in section 115 is set at a value of 80% of the limit velocity 336 m/s. In this setting, the influx gas velocity $q_p$ in a boundary area between first aerosol carrying pipe 107 and aerosol take-in section 115 is 338 m/s. Thus, the value of the influx gas velocity adequately useful in practical use is ensured.

In the above-mentioned configuration, the aerosol introduced to aerosol take-in section 115 in aerosol classification section 102 is initially composed of Si nm-sized fine particles and He medium gas. Then, the aerosol is mixed with argon (Ar) which is the carrier gas introduced from carrier gas introduction inlet 118. Therefore, the aerosol has a mixed gas of Ar and He as the medium gas, and such an aerosol is started being carried to fine-particle classification apparatus 112.

Next, when the above aerosol is passed through ionization chamber 117, Si nm-sized fine particles are charged by a radioactive ray radiated from radioactive isotope americium ($^{241}$Am) placed inside ionization chamber 117. The charging rate at this time depends on diameters of nm-sized fine particles and the pressure(mostly, the total pressure) inside second aerosol carrying pipe 114. In the first embodiment, the pressure inside second aerosol carrying pipe 114 is assumed to range from 10 to 100 Torr. Therefore, it is possible to charge Si nm-sized fine particles with a diameter of 5 nm to monovalence with the rate of about $10^{-5}$.

Next, the outline of operations in fine-particle classification apparatus 112 are explained. First, Ar gas as the sheath gas is introduced from sheath gas introduction inlet with a flow rate of 20l/min. The sheath Ar gas is flown to a space between outer cylinder 301 and inner cylinder 302 (which is the classification region 312 in the narrow sense) through filter mesh 313, so that the Ar gas can become the laminar flow effectively. At this point, the sheath gas with the flow rate almost equal to that of the influx sheath Ar gas is exhausted from sheath gas exhaustion outlets 305a and 305b with the rotary pump. The rotary pump is connected to the large-sized mechanical booster pump.

The medium gas is composed of the mixed gas of Ar and He. The aerosol containing the Si nm-sized fine particles is introduced to aerosol carrying pipes 114a and 114b. Next, the aerosols introduced to aerosol carrying pipes 114a and 114b are respectively passed through aerosol injection slits 306a and 306b. The aerosols passed through aerosol injection slits 306a and 306b are introduced to classification region 312. The aerosols introduced to classification region 312 are applied the radial electrostatic field around the common central axis by cathode high-voltage electrodes 310a and 310b attached on the outer wall of inner cylinder 302 and grounding electrodes 311a and 311b attached on the inner wall of outer cylinder 301.

Not-charged Si nm-sized fine particles, which are introduced from aerosol injection slits 306a and 306b to classification region 312, join the flow of the sheath gas with the laminar flow. Then, the not-charged Si nm-sized fine particles are carried from aerosol injection slits 306a and 306b to the directions to sheath gas exhaustion outlets 310a and 310b (from left to right in FIG. 3 from a viewer's point) to be exhausted from sheath gas exhaustion outlets 305a and 305b, respectively.

On the other hand, Si nm-sized fine particles charged in ionization chamber 117 are deflected by the electrostatic field formed in classification region 312. In particular, positive-charged Si nm-sized fine particles are deflected to the inner cylinder 302 side. A portion of the charged Si nm-sized fine particles are passed through aerosol take-in slits 307a and 307b, and then extracted from classified aerosol extraction outlet 309. The locus of charged fine particles in classification region 312 is determined fundamentally by the mobility of charged fine particles in the sheath gas, carrying velocity to horizontal direction by the sheath gas, distribution of electrostatic field strengths and geometric shapes (such as classification length L, the diameter of inner cylinder $R_1$ and the diameter of outer cylinder $R_2$). As actual operation parameters, the kind of sheath gas, flow rate of the sheath gas, sizes of charged fine particles, and valence of charged fine particles determine the locus. By setting such parameters appropriately, fine particles with a specific diameter can be extracted, thereby enabling the classification of the specific fine particles from the aerosol.

The central value of classified particle diameters is usually pre-determined by the horizontal-direction carrying velocity and the design of geometric shapes. Then, the electrostatic field strength is finally adjusted (as a variable parameter), thereby making it possible to select any classified particle diameter in some range. Actually, the classification accuracy at this point has a finite width of particle size distribution after classification due to a disorder of the sheath gas laminar flow caused by the influx of the carrier gas with a finite amount, a finite slit width, and effects of Brownian diffusion of nm-sized particles in the sheath gas.

In the first embodiment, as the geometric shape for the classification region, L is 20 mm, $R_1$ is 24 mm, and $R_2$ is 35 mm. Further, as the sheath gas, Ar gas with a flow rate of 20l/min is adopted. The applied voltage is variable in a range of 1 to 200V, and the positive-charged monovalent Si nm-sized fine particles are targets. According to the aforementioned settings, it is possible to determine the central value of diameters arbitrary in a range of 5 to 10 nm. As a result, 1.2 is achieved as the geometric standard deviation of the size distribution of classified particles.

Why Ar gas is used as the sheath gas is that Ar gas improves the resolution of classification as compared to He, in the same flow rate, because Ar gas has 1.68 times the molecular diameter σ as He and 1.13 times the viscosity coefficient μ as He. Further, Ar gas has the lowest price among inert gases. In the double-cylinder type DMA classification apparatus, it is possible to improve the classification resolution very effectively by setting the molecular diameter σ and viscosity coefficient μ of the sheath gas at greater values. The reason for this can be explained with the following equation (3) expressing the square of relative full width at half maximum (FWHM) of the size distribution of classified particles. The equation (3) is obtained by analyzing the behavior of the aerosol (fine particles and medium gas: carrier gas and sheath gas) in the classification region in the double-cylinder type DMA classification apparatus as the Brownian diffusion phenomenon on the basis of the kinetic theory of gas molecules.

$$FWHM^2 = const. \times \frac{\left(b+\frac{1}{b}\right)\frac{R_1}{R_2}(R_1+R_2)(kT)^2}{\mu \cdot \sigma^2 \cdot Q \cdot P \cdot d_p^2} \quad (3)$$

$$b = \frac{L}{R_2 - R_1}, const. \cong 2.784$$

It is premised that the classification resolution is proportional to the reciprocal of the relative full width at half maximum (FWHM), and the equation (3) is used. Thus, it is possible to derive the dependency on the classification resolution of each operation parameter such as flow rate of sheath gas Q, classification operation pressure P, and classification operation temperature T other than the molecular diameter σ and viscosity coefficient μ of the sheath gas. The results are summarized in Table 2, where k is the Boltzmann constant.

TABLE 2

| FLOW RATE OF SHEATH GAS Q | $Q^{0.5}$ |
|---|---|
| OPERATION PRESSURE ρ | $P^{0.5}$ |
| MOLECULAR DIAMETER OF SHEATH GAS σ | σ |
| PARTICLE DIAMETER OF FINE PARTICLE $d_P$ | $d_p$ |
| OPERATION TEMPERATURE T | $T^{-1}$ |

In the first embodiment, Ar gas with a great mass is used as the sheath gas besides He gas with a small mass that is needed in the generation of Si nm-sized fine particles. It is intended to improve the classification resolution by adopting a greater molecular diameter σ of the sheath gas. Further, the flow rate Q of the sheath gas is also set at a great value as possible to be contributed on the improvement of the classification resolution. The increase of classification operation pressure P is limited because the He gas pressure in the generation of Si nm-sized fine particles is low (10.0 Torr). In other words, the classification operation pressure P is limited by the structure of aerosol take-in section 115. Further, it is effective to set the operation temperature at a lower value to improve the classification resolution. However, since it costs much to cool the whole apparatus actually, the operation temperature is set at a room temperature. Finally, as the diameter of target fine particles ($d_p$) is decreased, the classification resolution tends to be lowered. Therefore, it is necessary to carefully design the DMA classification apparatus for nm-sized fine particle with a diameter of several nm, specifically, less than 5 nm.

The high-purity semiconductor fine particles classified in fine-particle classification apparatus 112 illustrated in FIG. 3 are next carried to deposition chamber 121 illustrated in FIG. 4 along with the carrier gas with the constant flow rate Qa through fine-particle deposition nozzle 119. Then, the classified particles are collected and deposited on deposition substrate 402. At this time, transparent medium target 408 is excited by excimer laser beam 405. The excited transparent medium target 408 is ejected by the ablation reaction. At the same time as high-purity semiconductor fine particles are collected and deposited on deposition substrate 402, ejected transparent medium is collected and deposited on deposition substrate 402.

At this point, it is possible to deposit the transparent medium under optimal conditions by control the pressure inside deposition chamber 121 to hold the constant pressure P2 using carrier gas differential-evacuation system 123.

By carrying out the collections and depositions of the classified high-purity semiconductor fine particles and transparent medium at the same time, it is possible to form a structure where group IV semiconductor fine particles 602 are dispersed in semiconductor fine particles dispersed transparent medium layer 601 on deposition substrate 402 with the surface on which lower electrode layer 606 is formed. Lower electrode layer 606 is formed by, for example, sputtering, on deposition substrate 402. Further, lower electrode layer 606 is composed of, for example, metal silicide, and has high chemical and thermal stabilities.

Figure 6A:
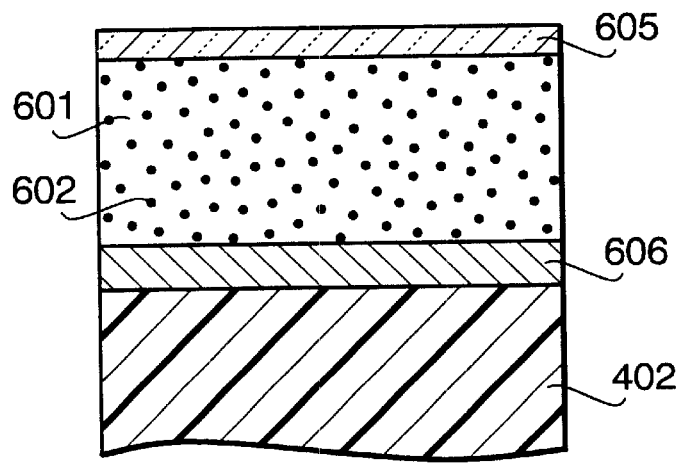
FIG. 6A is an enlarged sectional view of a first functional material produced in the functional material production apparatus illustrated in FIG. 1.
Figure 6B:
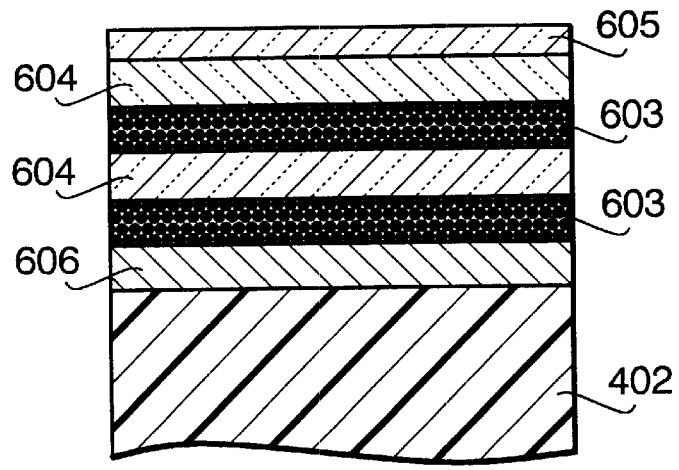
FIG. 6B is an enlarged sectional view of a second functional material produced in the functional material production apparatus illustrated FIG. in 1.

In addition, in the first embodiment, the collections and depositions of the high-purity semiconductor fine particles and transparent medium are performed at the same time in deposition chamber 121 illustrated in FIG. 4. On the contrary, it is possible that the deposition of high-purity semiconductor fine particles is first carried out with fine-particle deposition nozzle 119 to deposit a constant amount of high-purity semiconductor fine particles, and that the transparent medium is deposited on the deposition substrate, so as to form a layered structure of fine particles and transparent medium. Further, by repeating the deposition of high-purity semiconductor fine particles and that of transparent medium alternately a plurality of times, it is possible to form a structure, as illustrated in FIG. 6B, where group IV semiconductor fine particles layer 603 and transparent medium layer 604 are piled in the form of layers.

In addition, in the first embodiment, the structure, where group IV semiconductor fine particles 602 are dispersed in transparent medium layer 601, is directly formed on deposition substrate 402. It may be also possible to form an appropriate medium layer on deposition substrate 402, and to form semiconductor fine particles dispersed transparent medium layer 601, in which group IV semiconductor fine particles 602 are dispersed, on such a medium layer.

At the same time as the collection and deposition of high-purity semiconductor fine particles, it is possible to perform the confirmation and control of a deposition amount of fine particles using minute-ampere meter 124. Minute-ampere meter 124 measures the transfer of charged particles carried out when the classified charged fine particles are collected and deposited on the deposition substrate, as the confirmation and control of the deposition amount of fine particles.

After the collection and deposition of high-purity semiconductor fine particles and that of transparent medium are finished, transparent medium target 408 is exchanged with Transparent electrode material target 409 using the target drive exchange mechanism 406 illustrated in FIG 4.

Transparent electrode material target 409 is excited by excimer laser beam 405, and ejects the transparent electrode species by the ablation reaction. The ejected transparent electrode species form transparent electrode layer 605 on semiconductor fine particles dispersed transparent medium layer 601 or transparent medium layer 604. At this time, the kind of ambient gas and the pressure P2 inside deposition chamber 121 are controlled to enable the transparent electrode species to be deposited under optimal conditions as a thin film (for, example, the ambient gas is $O_2$ with a purity of 99.999%, the pressure is in a range of 10 to 200 mTorr).

As described above, it is possible to form the transparent electrode to be contacted to the optical functional element in a single apparatus with contamination and damages reduced without exposing an active region of the functional material to the atmosphere.

In addition, the deposition of transparent medium and transparent electrode material are carried out by the ablation by the laser beam. However, it may be possible to carry out the deposition of transparent medium target 408 and transparent electrode material target 409 by sputtering. When the deposition is carried out by the sputtering, it is possible to use the technique in the conventional semiconductor apparatus, and therefore to simplify mechanism parts and optical parts. Since the sputtering is carried out in mixed background gases of Ar as a main component and $O_2$ as a second component with a pressure of several Torr to several mTorr, it is possible to reduce the effects of oxidation on semiconductor materials in forming transparent electrode layer 605 in particular. As described above, it is effective to carry out the deposition by the sputtering.

Figure 7:
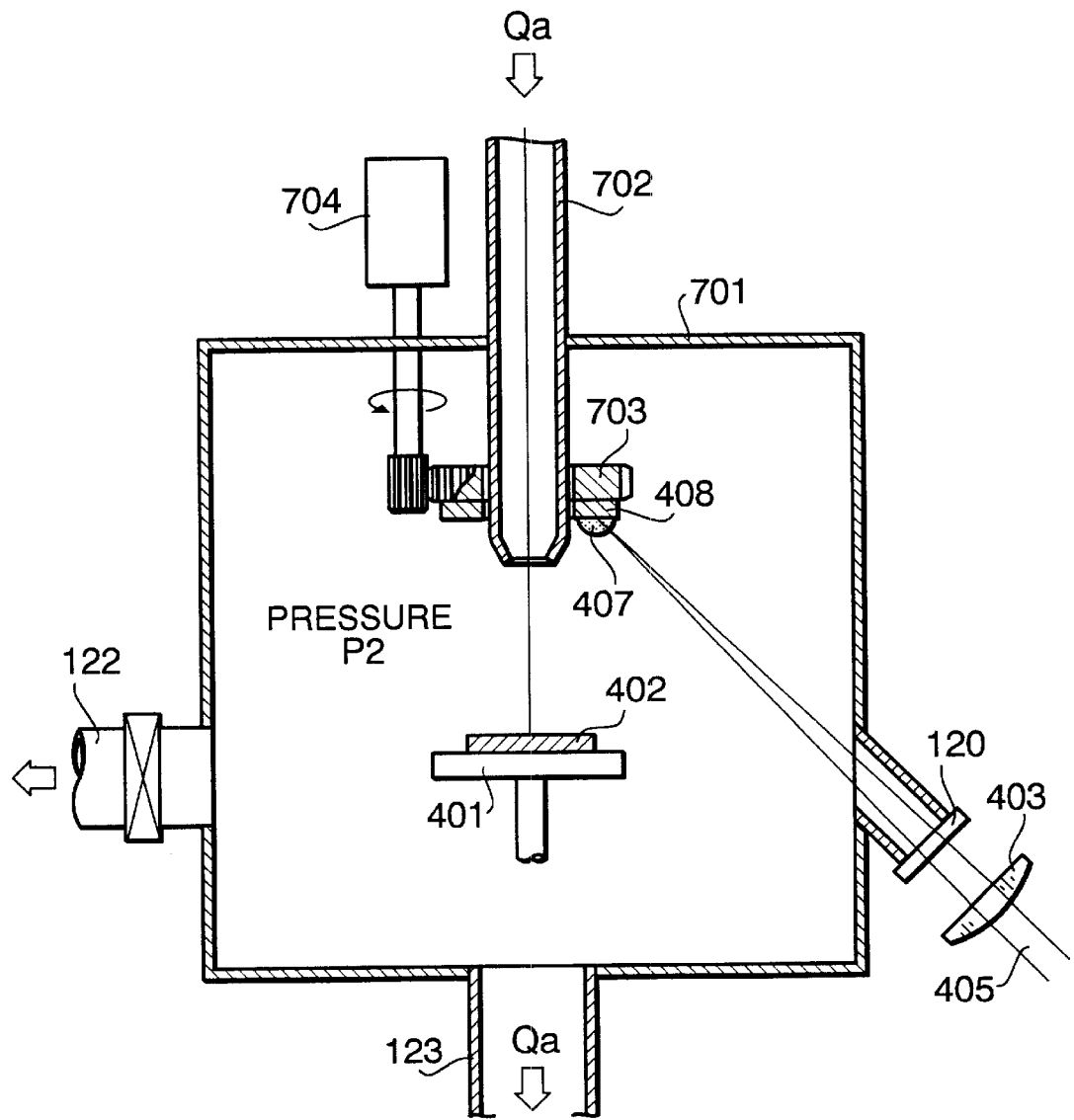
FIG. 7 is a diagram illustrating a configuration of another example of the deposition section in the functional material production apparatus illustrated FIG. in 1.

A deposition chamber which is modified based on the first embodiment is explained using FIG. 7. FIG. 7 is a configuration diagram of the deposition chamber modified based on the first embodiment. In addition, in FIG. 7, the same sections as those already explained have the same symbols to omit the explanation thereof.

As illustrated in FIG. 7, fine-particle deposition nozzle 702 is provided at almost the center on an upper portion in deposition chamber 701. The classified fine particles are entering and injected inside deposition chamber 701 along with the carrier gas with the constant flow rate $Qa$ from fine-particle deposition nozzle 702.

Deposition substrate 402 is placed at almost the center inside deposition chamber 701. Deposition substrate 402 is fixed to deposition substrate holder 401. Therefore, an injection hole of fine-particle deposition nozzle 702 is positioned to a direction of the normal line of deposition substrate 402.

Transparent medium target 408 is fixed to target holder 703. Target holder 703 performs the drive of the target with motor 704. Transparent medium target 408 is excited by excimer laser beam 405. Excited transparent medium target 408 generates ablation plume 407. The target holder 703 is placed in such a manner that the growth direction of ablation plume 407 matches the direction of the normal line of deposition substrate 402. Further, transparent medium target 408 is made in the form of a ring.

By thus configuring the inside of deposition chamber 701, the deposition of high-purity semiconductor fine particles and that of transparent medium are both carried out on deposition substrate 402 from the normal direction thereof, whereby the deposition e yields of both high-purity semiconductor fine particles and transparent medium are improved. Further, it is possible to obtain a uniform distribution of deposited species composed of high-purity semiconductor fine particles and transparent medium.

Figure 8A:
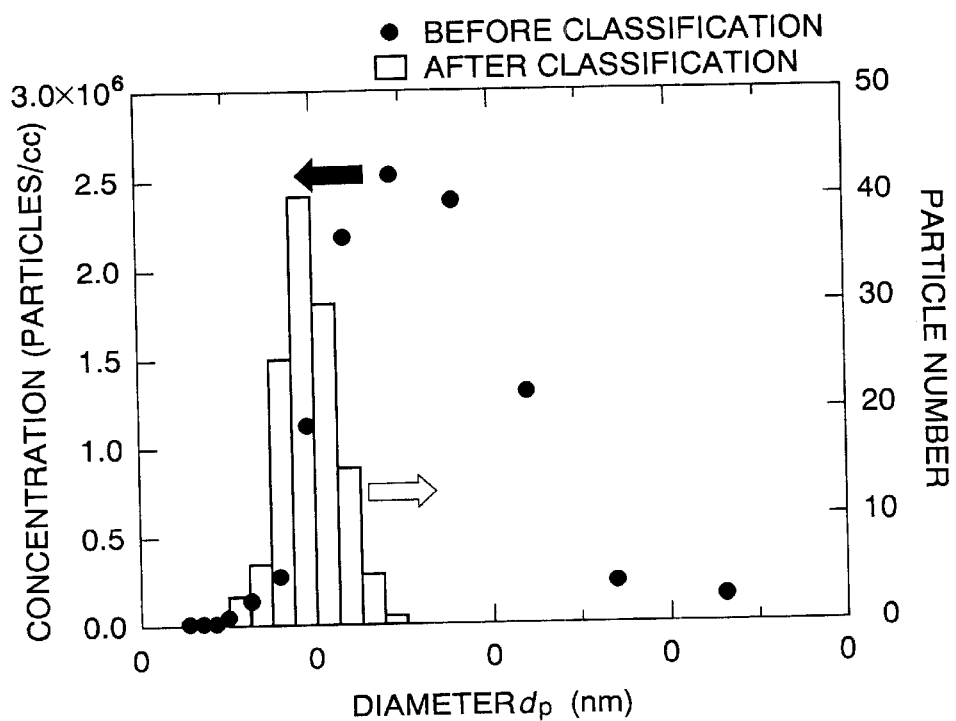
FIG. 8A is a diagram illustrating a particle size distribution of fine particles after being generated, and that of fine particles after being classified.

Next, FIG. 8A illustrates an example of a particle size distribution of nm-sized Si fine particles which were actually generated using the apparatus system according to the first embodiment. The classification and deposition conditions at that time are as follows:

Generation chamber He gas pressure:5.0 Torr; deposition chamber He gas pressure:4.5 Torr; flow rate of carrier gas:He 0.33SLM (Standard conditions, 1/min); flow rate of sheath gas:He 1.67SLM; DMA classification region applied voltage:–2.5V; deposition substrate applied voltage:–100V; and deposition substrate temperature:room temperature. The other conditions with respect to Si fine particles generation such as irradiation conditions of an excited laser are all the same as described previously in the detailed explanation for FIG. 2 in the first embodiment.

In FIG. 8A, the particle size distribution (hereinafter, also referred to as size distribution) of Si fine particles immediately after being generated is expressed with black circles, and that of Si fine particles after being classified are expressed with white histograms. The particle size distribution of Si fine particles immediately after being generated was calculated based on measured values by minute-ampere meter 124 due to incidence of charged particles at deposition substrate holder 401, while sweeping the DMA classification region applied voltage (electrostatic field strength). The particle size distribution of classified fine particles was obtained with an electron microscope by observing Si fine particles deposited on substrate deposition 402 under the fixed DMA classification region applied voltage (–2.5V).

The size distribution of the generated Si fine-particles is extremely broad (black circles: geometric standard deviation $\sigma_g$=1.8). However, by performing the DMA classification for the Si fine-particles, it is possible to obtain an extremely sharp size distribution (white histograms:geometric standard deviation $\sigma_g$=1.2). Such a sharp size distribution is called monodispersed diameter particles In addition, in FIG. 8A, the average particle diameter of the Si fine-particle group immediately after being generated is 5.8 nm. Further, by maintaining the DMA classified region applied voltage at −2.5V, it is possible to obtain a smaller average particle diameter of 3.8 nm after the classification.

It is known in the semiconductor from the principle in quantum mechanics that the energy band gap $E_g$ of a semiconductor fine particle varies as a function of the particle diameter $d_m$ thereof when the particle diameters are synthesized in regions comparable to Bohr radiuses of excitons or de Broglie wavelengths of carriers. In other words, $E_g$ increases with decreasing $d_m$. In the case where the material of fine particles is Si, it is confirmed that when $d_m$ ranges from 2 to 10 nm, $E_g$ varies in the visible region such as a range from 1.7 to 3.0 eV, by the analysis obtained by combining effective-mass approximation and tight-binding approximation. $E_g$ is exactly a physical quantity for determining photon energies of optical absorption.

Figure 8B:
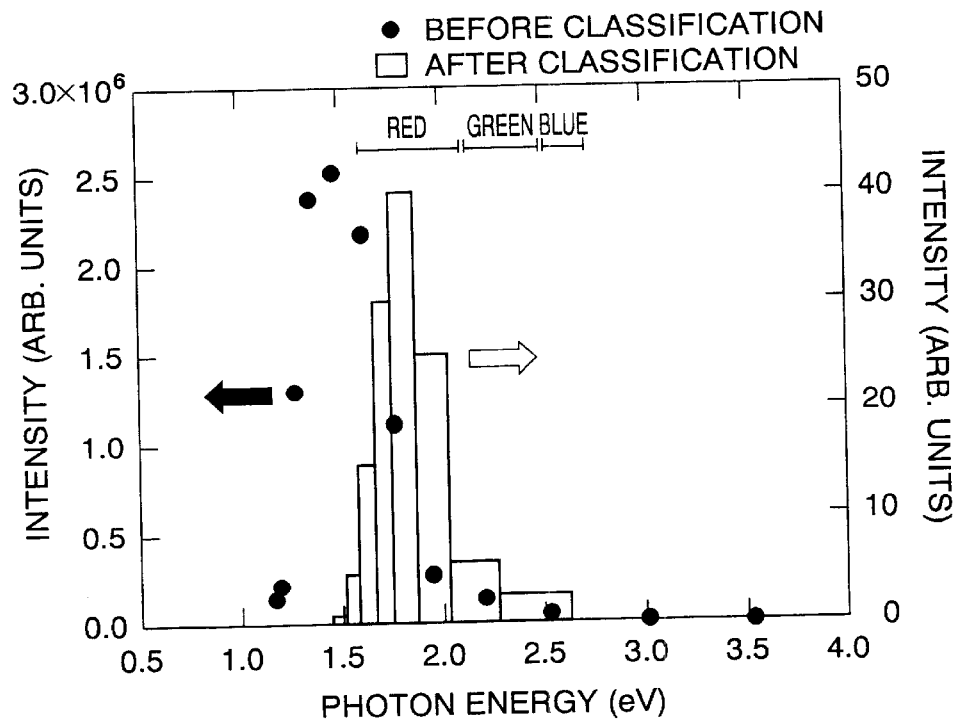
FIG. 8B is a diagram illustrating an optical gap distribution of fine particles after being generated, and that of fine particles after being classified.

FIG. 8B illustrates a diagram of the distributions of $E_g$ corresponding to size ($d_m$) distributions of Si fine particles before and after the classification in FIG. 8A. As can be seen from FIG. 8B, the center of the $E_g$ distribution of Si fine-particle group immediately after being generated (before the classification, black circles) is in the near-infrared region (1.4 eV). The photon energy of 1.4 eV corresponds to the diameter of 5.8 nm in FIG. 8A. On the contrary, the center of the $E_g$ distribution of Si fine-particle group after being classified (white histograms) is in a wavelength region for the red portion in the visible region (1.8 eV). The photon energy of 1.8 eV corresponds to the diameter of 3.8 nm in FIG. 8A. It is understood from the aforementioned phenomenon that it is impossible to provide the Si fine particle group immediately after being generated with the optical function in the visible region, but it is possible to provide the Si fine-particle group with the optical function (such as optical absorption and light emission) in the visible region by subjecting such a Si fine-particle group to the DMA classification. Enabling Si fine-particle group to exhibit the optical function (such as optical absorption and light emission) is extremely valuable in industries.

As described above, it is possible to make fine particles be in the monodispersed state by classifying the Si fine particles immediately after being generated. When the fine particles are thus in the monodispersed state, in other words, the peak is present at a specific particle diameter in the size distribution, the energy band gaps corresponding to the diameters are also made uniform. Therefore, since a large number of classified fine particles are present, the fine particles emit a light strongly with a wavelength corresponding to the energy band gap. By classifying the fine particles to the diameter corresponding to the band gap energy which is the wavelength of the visible region, it is possible to achieve the fine particles exhibiting the optical function in the visible region. In addition, the relationship between particle diameter and energy band gap varies depending on materials for semiconductor because the de Broglie wavelength varies depending on the materials.

Further, it is possible to produce optical functional devices with desired wavelengths by classifying the Si fine-particle group with desired diameters, by using that $E_g$, determining wavelengths for optical absorption and light emission, as a function of the particle diameter $d_m$ of the Si fine particles. In other words, it is possible to produce the optical functional devices in the visible region by depositing the classified Si fine-particles with the selected monodispersed diameters, on deposition substrate 402.

Figure 9A:
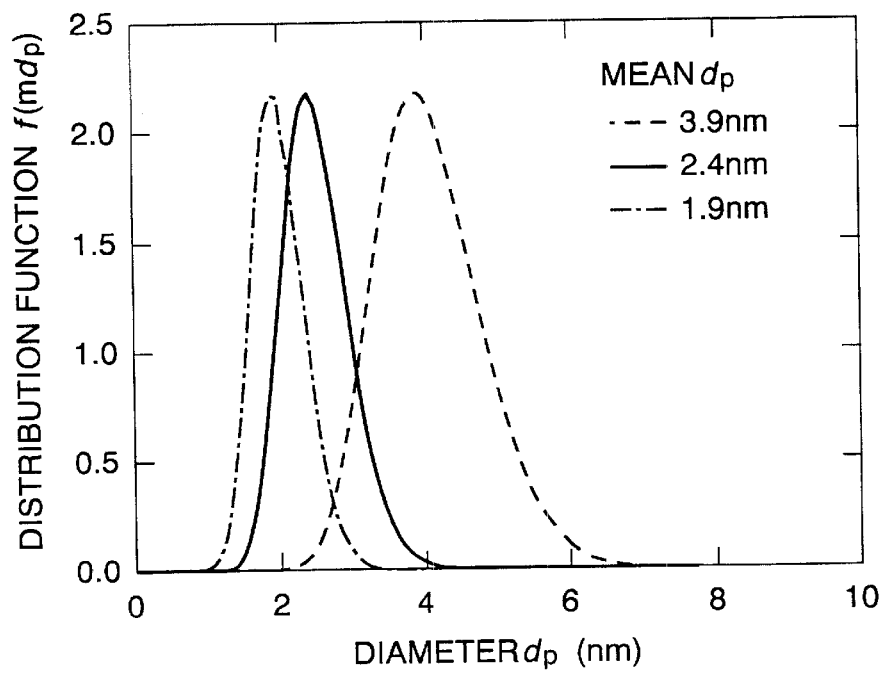
FIG. 9A is a diagram illustrating a particle size distribution of three kindsof Si fine-particle groups produced for multicolor (three primary colors) optical functions.
Figure 9B:
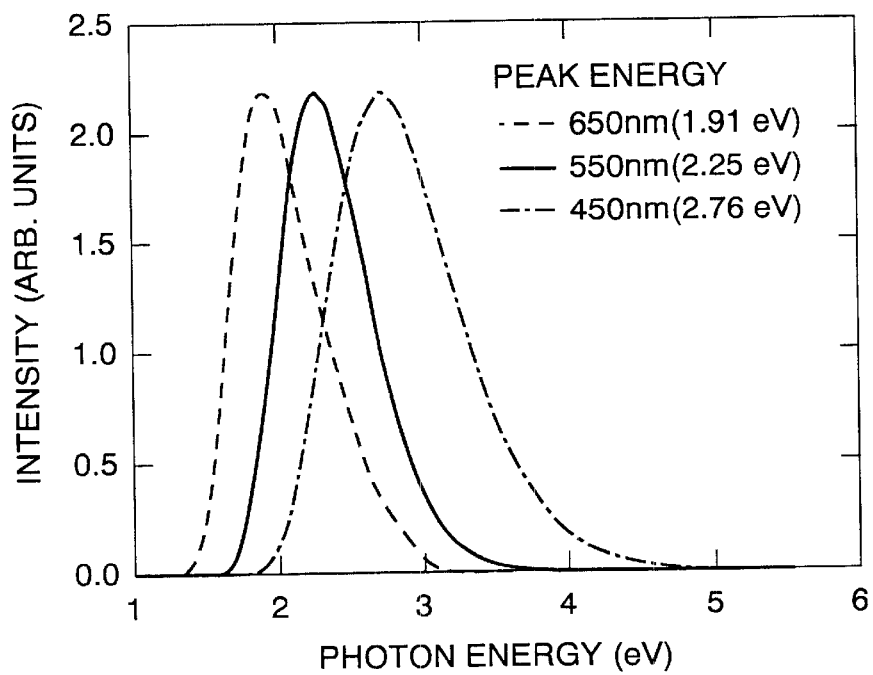
FIG. 9B is a diagram illustrating a particle size distribution of three kinds of Si fine-particle groups produced for multicolor (three primarily colors) optical functions.

Using the generation-classification-deposition sequential process system in the first embodiment, three Si fine-particle groups illustrated in FIG. 9A were produced. These Si fine-particle groups were classified respectively setting the average diameter at 3.9 nm, 2.4 nm and 1.9 nm. $\sigma_g$ of each Si fine-particle group is within 1.2. The determination of the average diameter of Si fine-particle group can be carried out by controlling the DMA classification region applied voltage. By applying the same analysis as in FIG. 8, three Si fine-particle groups that the central values in $E_g$ (corresponding photon energy) distributions correspond to 1.91 eV, 2.25 eV and 2.76 eV (FIG. 9B). The values of $E_g$ correspond to wavelengths of 650 nm, 550 nm and 450 nm, respectively. These wavelengths are exactly for the three primary colors, i.e., for red, green and blue. It is thus possible to produce the optical functional devices with emitting wavelengths for red, green and blue by depositing the classified Si fine-particle groups with such a diameter co-deposited on substrate 402, with the medium, by the pulsed laser ablation in inert background gases.

As described above, the achievement of the optical functional element emitting three primary colors in the visible region using Si fine particles has an extremely great significance in optical and electronic industries.

As described above, the first embodiment has the configuration for flowing the carrier gas with a large gas velocity to aerosol take-in section 115 to introduce the aerosol to aerosol classification section. 102. Thus, the static pressure in aerosol take-in section 115 is lowered. As a result, even when the total pressure in aerosol take-in section 115 configured at the side of aerosol classification section 102 is set at a value equal to or higher than the total pressure in aerosol generation section 101, the static pressure in aerosol take-in section 115 can be made lower than the total pressure in aerosol generation section 101. Accordingly, it is possible to introduce the aerosol from aerosol generation section 101 to aerosol classification section 102 with the total pressure equal to or higher than that in aerosol generation section 101.

Further, in the first embodiment, the specific carrier gas is flown to aerosol take-in section 115 configured at the side of aerosol classification section 102, and the diameter of aerosol take-in section 115 is designed to be smaller than the diameters of other pipes connected to a front portion and rear portion thereof, whereby the gas velocity of carrier gas is locally increased in aerosol take-in section 115. As a result, it is possible to lower the static pressure in aerosol take-in section 115 at the side of aerosol classification section 102 effectively without preparing a specific take-in apparatus.

Further, the first embodiment has the constitution where introduced as the carrier gas or sheath gas inside aerosol classification section 102 is the medium gas of which the kind is different from that of the medium gas inside aerosol generation section 101, in particular, the medium gas with a mass larger than that of the medium gas inside aerosol generation section 101. It is thereby possible to lower the static pressure in aerosol take-in section 115 in aerosol classification section 102 further effectively. As a result, it is possible to introduce the aerosol to aerosol classification section 102 more efficiently. Further more, since the mass of the medium gas (carrier gas or sheath gas) inside fine-particle classification apparatus 112 is heavy, it is possible to suppress the spacial dissipation by Brownian diffusion of target fine particles in fine-particle classification apparatus 112, resulting in the further improved classification accuracy in aerosol classification section 102.

In addition, in the first embodiment, when the fine particles, which are gene rated from semiconductor target 205 then classified, are collected on deposition substrate 402, substantially at the same time, the species generated by the ablation reaction on transparent medium target 408 are collected on deposition substrate 402. It is thereby possible to disperse the classified fine particles generated from semiconductor 205 in the species composed of transparent medium target 408 to deposit. As a result, it is possible to produce the high-purity fine particles with the monodispersed diameter and uniform structure efficiently with contamination and damages reduced, and to deposit such high-purity fine particles on the substrate at the same as the deposition of the transparent medium. Thus, it is possible to compose the form and structure of high quality optical functional devices.

Further, in the first embodiment, it is possible to alternately deposit a thin film composed of classified fine particles generated from semiconductor target 205 and another thin film composed of transparent medium target 408. As a result, it is possible to produce the high-purity fine particles with the monodispersed diameter and uniform structure efficiently with reducing contamination and damages, and to deposit such high-purity fine particles and the transparent medium alternately on the substrate.

In addition, fine-particle classification apparatus 112 according to the first embodiment adopts the type electric mobility classification apparatus. It is thereby possible to classify fine particles with a high yield. As a result, the high-purity fine particles with a monodispersed diameter and uniform structure can be collected and deposited efficiency.

Further, according to the first embodiment, it is possible to hold the pressure inside fine-particle generation chamber 104 at the optimal pressure for the condensation and growing of fine particles generated from semiconductor target 205. It is also possible to hold the pressure inside deposition chamber 121 at the optimal pressure for the deposition of species generated from transparent medium target 408. It is thereby possible to generate and deposit the fine particles and transparent medium under respective optimal ambient gas pressures. Furthermore, it is possible to cause a pressure difference between aerosol generation section 101 and deposition section 103. By the use of the generated pressure difference, it is possible to carry the fine particles from aerosol generation section 101 to deposition section 103 efficiently.

In addition, according to the first embodiment, it is possible to exchange transparent medium target 408 with transparent electrode material target 409 using target drive exchange mechanism 406 provided at deposition chamber 121. It is thereby possible to excite transparent electrode material target 409 after depositing the species composed of semiconductor target 205 and transparent medium target 408. Then, it is possible to deposit species generated by the ablation reaction caused by the excited transparent electrode material target 409 on the species composed of semiconductor target 205 and transparent medium target 508 to form a transparent electrode. As a result, it is made possible to also form the transparent electrode to be contacted to the optical functional devices in a single apparatus with reducing contamination and damages without exposing the active region of he functional functional materials to the atmosphere.

Further, in the modification example on the basis of the first embodiment, it is possible to carry out the deposition of species composed of semiconductor target 205 and transparent medium target 408 on the substrate from the normal direction to the substrate, thereby making it possible to improve the yields of stacking and deposition to the substrate of the fine particles and transparent media.

In addition, the first embodiment has ionization chamber 117 adopting a charging system for target fine particles using the radioactive isotope. Further, the charging efficiency can be improved by using a vacuum ultraviolet light source to charge the fine particles in ionization chamber 117.

In addition, in the first embodiment, the generated fine particles are charged in the ablation plume generated by the excitation pulse laser. Therefore, it is possible to eliminate ionization chamber 117 where the radioactive isotope and vacuum ultraviolet ray source are used. Thus, it is possible to perform the miniaturization and cost reduction of the apparatus, and further to shorten the process of carrying fine particles. As a result, it is possible to suppress the phenomena such as deposit and aggregation of fine particles being carried.

Further, in the first embodiment, it may be possible to carry out the deposition of transparent medium target 408 and transparent electrode material target 409 by sputtering. It is thus possible to use the technique in the conventional semiconductor apparatus, and to further simplify mechanical parts and optical parts.

Second Embodiment

A functional material production apparatus according to the second embodiment of the present invention is explained. The apparatus is obtained by modifying the fine-particle classification apparatus according to the first embodiment to be operated in a pressure lower than the atmospheric pressure. In order to operate the fine-particle classification apparatus in the pressure lower than the atmospheric pressure, it is necessary to exhaust a sheath gas inside the fine-particle classification apparatus efficiently with a high exhaustion rate.

In the second embodiment, in order to achieve the subject, it is noticed that an increase of the cross-section area of the classification region in the fine-particle classification apparatus is efficient. Actually, in order to increase the cross-section area of the classification region in the fine-particle classification apparatus, the form of the cross section of the fine-particle classification apparatus is modified from the double-cylinder type to a rectangle type.

In addition, the sections and chambers in the second embodiment are the same as in the first embodiment except the fine-particle classification apparatus, and explanations thereof are omitted.

Figure 10A:
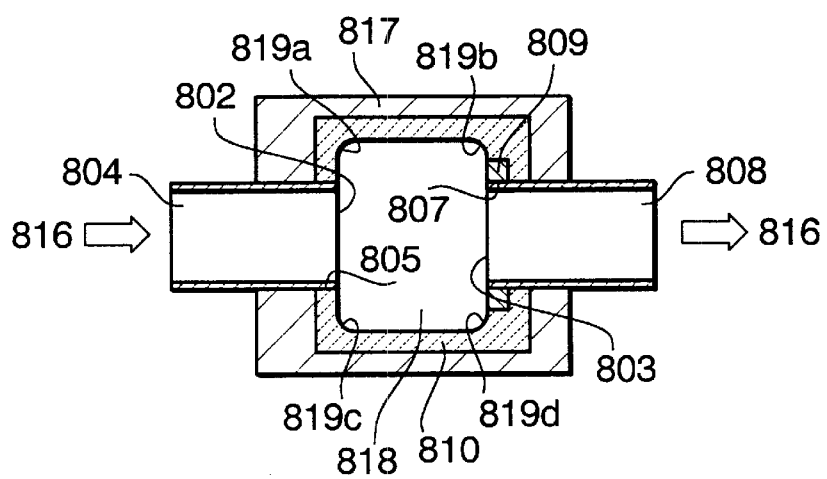
FIG. 10A is a horizontal sectional view of a fine-particle classification apparatus according to a second embodiment of the present invention.
Figure 10B:
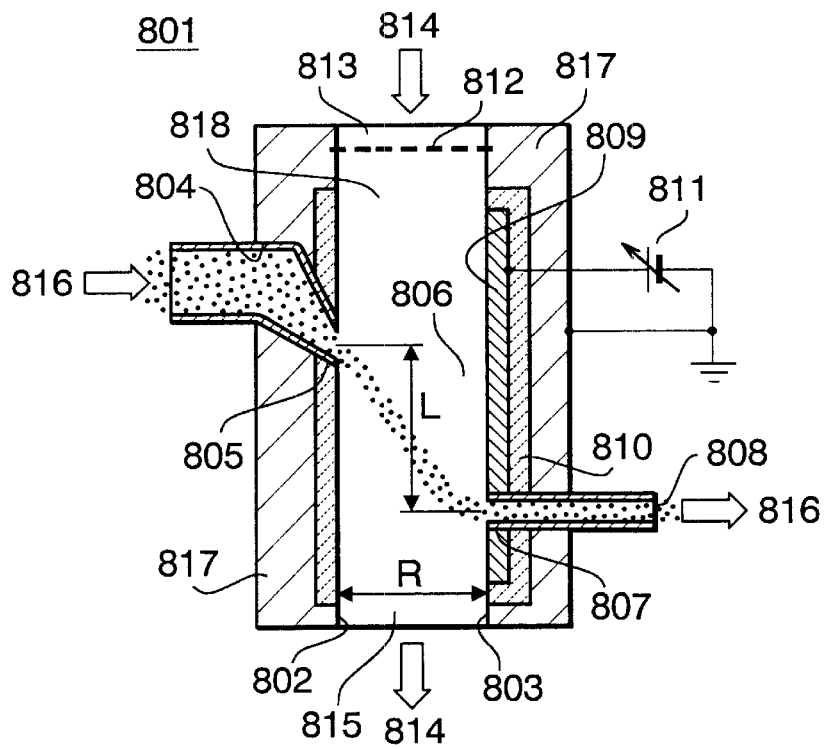
FIG. 10B is a longitudinal sectional view of the fine-particle classification apparatus according to the second embodiment of the present invention.
Figure 11:
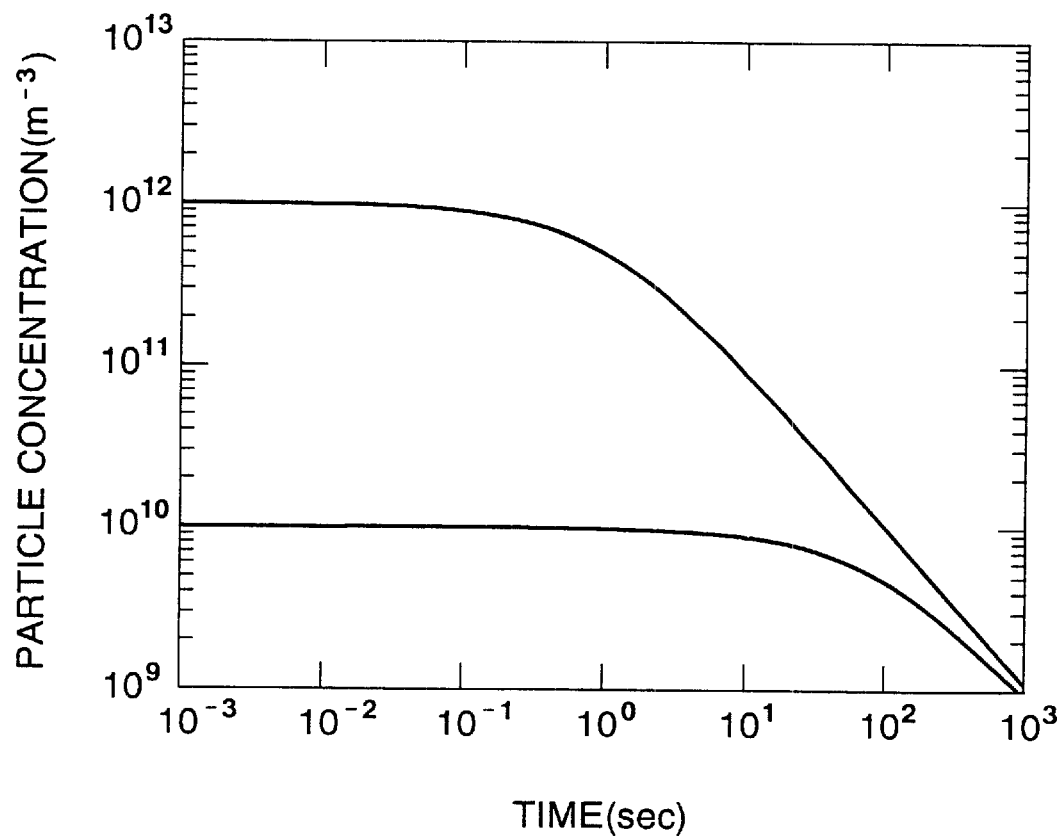
FIG. 11 is a diagram illustrating a time-dependency of the particle concentration of fine particles with an initial diameter of 10 nm floating in the gas.

The fine-particle classification apparatus according to the second embodiment is next explained using FIG. 10A and FIG. 10B. FIG. 10A and FIG. 10B are configuration diagrams of the fine-particle classification apparatus according to the second embodiment.

Fine-particle classification apparatus 801 has the cross-section in the form of a rectangle, and is composed of outer shell portion 817 with space portion 818 of which the form of the cross-section is nearly rectangle. Flat portions A802 and B803 are formed in parallel to each other on respective inner surfaces at left and right sides in outer shell portion 817, being faced to each other with a constant interval R. The forms of flat portions A802 and B803 are both rectangles.

Provided at a slightly upper portion than the center in the side of flat portion A802 of outer shell portion 817 is carrier gas introduction inlet 804 for introducing the carrier gas which carries the charged fine particles. Provided near carrier gas introduction inlet 804 at the side of flat portion A802 of Outer shell portion 817 is carrier gas injection outlet 805 for injecting the introduced carrier gas to classification region 806.

Classification region 806 is a space with a constant interval R between flat portions A802 and B803 of space portion 818 inside outer shell portion 817. In addition, carrier gas injection outlet 805 is provided at a higher portion in classification region 806 of outer shell portion 817.

Provided at a side surface at the side of classification region 806 at the side of flat portion B803 of outer shell portion 817 is slit 807 for selecting fine particles with a monodispersed diameter. Provided at an outer side surface of outer shell portion 817 near slit 807 is carrier gas exhaustion outlet 808 to extract the selected fine particles with the monodispersed diameter.

In addition, metal plate 809 is provided on a side surface, at the side of classification region 806, of outer shell portion 817. In other words, a portion of flat portion B803 is composed of metal plate 809. Metal plate 809 is surrounded with insulator 810 being contacted thereto, whereby metal plate 809 is completely insulated by insulator 810. In addition, insulator 810 is provided to shield an inside portion of outer shell portion 817 except a portion of flat portion B803 in outer shell portion 817.

DC power supply 811 is connected to the side surface at the side of flat portion B803 in outer shell portion 817. The outer of outer shell portion 817 is grounded by DC power supply 811. Metal plate 809 is applied a positive or negative voltage by DC power supply 811.

Filter 812 is provided at an upper stream portion than classification region 806 in fine-particle classification apparatus inside outer shell portion 817. Filter 812 makes the sheath gas, introduced from sheath gas introduction inlet 813, a uniform laminar flow.

The fine particle classification operation in fine-particle classification apparatus 801 is next explained.

Sheath gas 814 is introduced to fine-particle classification apparatus 801 through sheath gas introduction inlet 813, and then passed through filter 812. By being passed through filter 812, the flow of sheath gas 814 in fine-particle classification apparatus 801 is made uniform.

After being passed through filter 812, sheath gas 814 is passed through classification region 806 in a state of laminar flow, and then exhausted from sheath gas exhaustion outlet 815. On the otherhand, charged fine particles are carried by carrier gas 816, and introduced to fine-particle classification apparatus 801 from carrier gas introduction inlet 804. Carrier gas 816 introduced to fine-particle classification apparatus 801 is injected to classification region 806 from carrier gas injection outlet 805.

In classification region 806, the electrostatic field is applied to a space between flat portions A802 and B803 in a direction vertical to the flow of sheath gas 814. Therefore, the fine particles injected from carrier gas injection outlet are carried downward, while indicating the deflected loci in a direction from flat portion A802 to flat portion B 803. The loci are the deflection corresponding to the degree of electric mobility which depends on the number of charged fine particles and the diameter of fine particles. Then, only particles reaching slit 807 provided at the lower portion of flat portion B803 are extracted from carrier gas exhaustion outlet 808 as classified fine particles.

In order to improve the classification resolution in fine-particle classification apparatus 801, it is necessary that the sheath gas passed through classification region 806 be in a laminar flow state. In order to achieve the laminar flow state, as a form of the cross section, it is desired to avoid a form with acute angles which tend to generate stagnation. It is further desired that the form of the cross section of classification region 806 be smooth curved lines as possible. Accordingly, four corners 819*a* to 819*d* of the cross section of classification region 806 in rectangle type fine-particle classification apparatus 801 are cut to be circles. It is thereby possible to generate further uniform laminar flow state of sheath gas 814. As a result, it is made possible to improve the classification resolution of fine particles in fine-particle classification apparatus 801.

In addition, generally, an exhaustion conductance of a pipe is proportional to the square of the cross-section area of the pipe in the viscous flow area. Therefore, the cross-section area of classification region 806 in fine-particle classification apparatus 801 is set at a value equal to or more than that of the sheath gas pipe at the upper stream portion than sheath gas introduction inlet 813. Thus, the conductance of classification region 806 in fine-particle classification apparatus 801 is set at a value equal to or more than that of the sheath gas pipe at the upper stream portion than sheath gas introduction inlet 813. As a result, it is possible to eliminate stagnation in sheath gas 814 flown to classification region 806 through sheath gas introduction inlet 813 from the sheath gas pipe. Further, it is made possible that sheath gas 814 passed through classification region 806 becomes the laminar flow state.

Further, the form of the cross section of the sheath gas pipe at the upper stream portion than sheath gas introduction inlet 813 is designed to be continuously changed to the form of the cross section of classification region 806 in fine-particle classification apparatus 801. It is thereby possible to prevent rapid changes of the form of a sheath gas pass in front and rear portions of sheath gas introduction inlet 813. As a result, it is made possible that stagnation and disorder of the sheath gas flow are suppressed, and that the sheath gas passed through classification region 806 becomes the laminar flow state. In other words, it is made possible to achieve fine-particle classification apparatus 801 with excellent classification performance.

In particular, when the cross-section area of classification region 806 in fine-particle classification apparatus 801 is equal to that of the sheath gas pipe at the upper stream portion than sheath gas introduction inlet 813, it is important that the changes of the form of the sheath gas pass around sheath gas are made smooth and continuous in the front and rear portions of sheath gas introduction inlet 813. The reason for this is that making the changes of the form of the sheath gas pass smooth and continuous in the front and rear portions of sheath gas introduction inlet 813 is extremely effective to the flow of the sheath gas keeps the laminar flow state.

In addition, in order to operate fine-particle classification apparatus 801 at a pressure lower than the atmospheric pressure, it is necessary to exhaust the sheath gas with a high exhaustion rate. Alternately, in order to operate fine-particle classification apparatus 801 at a pressure lower than the atmospheric pressure, it is necessary to exhaust the sheath gas efficiently with sheath gas differential-exhaustion system 126 illustrated in FIG. 1.

To solve the above problem, in fine-particle classification apparatus 801 according to the second embodiment, the form thereof is modified to a rectangle type. It is thereby achieved to obtain the fine-particle classification apparatus in which the cross-section area of classification region 806 in fine-particle classification apparatus 801 is decreased to a value almost equal to that of the cross-section area of the sheath gas pipe at the upper stream portion than the sheath gas introduction inlet. As a result, it is possible to decrease the sheath gas capacity inside fine-particle classification apparatus 801 considerably. Further, the low pressure operation in fine-particle classification apparatus 801 is achieved by exhausting the sheath gas efficiently with sheath gas differential-exhaustion system 126 composed of a small-sized vacuum pump.

Specifically, as the sheath gas pipe at the upper stream portion than sheath gas introduction inlet 813 illustrated in FIG. 10, for example, a cylinder pipe with a diameter of 0.5 inch (about 12.7 mm) is used. Further, the cross-section area of classification region 806 in fine-particle classification apparatus 801 is decreased to the value (about 130 mm$^2$) almost equal to that of the cross-section area of the sheath gas cylinder pipe. Furthermore, projection length L between carrier gas injection outlet 805 and slit 807 is set at 20 mm. The sheath gas capacity inside fine-particle classification apparatus 801 is made one-two hundredth that of fine-particle classification apparatus 112 according to the first embodiment. As a result, even when a small-sized vacuum pump with a rate of 130 l/min is used as a pump composing sheath gas differential-exhaustion system 126, it is made possible to operate the fine-particle classification apparatus 801 at a low pressure in a range of 20 to 50 Torr.

In addition, the four corners of the cross section, which is a rectangle, of classification region 806 in fine-particle classification apparatus 801 are cut to be circles, so that the cross section of sheath gas cylinder pipe, which is a circle, is continuously changed to the cross section of classification region 806. By thus avoiding the rapid changes of the form of gas path in the front and rear portions of sheath gas introduction inlet, disorders in the sheath gas flow are suppressed and the laminar flow thereof is held.

The fine particles introduced to fine-particle classification apparatus 801 by second aerosol carrying pipe 114 illustrated in FIG. 1 are extracted from classified aerosol extraction outlet 309. The carrying time of fine particles spent by the detection thereof at Minute-ampere meter 124 depends on the flow rate of the carrier gas and that of the sheath gas.

Generally, fine particles floating in a gas cause the collision and aggregation thereof due to the effect of Brownian diffusion. The diameter of the fine particles are thereby increased as time passes. Further with the aggregation of fine particles, the particle concentration of the fine particles floating in the gas is decreased. Basically, in the case where the initial diameters of the fine particles are uniform, the particle concentration of the fine particles is decreased in inverse proportion to the time. In the case where the initial particle concentration of fine particles floating in the gas is large, the ratio of aggregation thereof is also large. As a result, the dependency of the particle concentration on the time and initial particle concentration is expressed as that a difference between the reciprocal of the initial particle concentration and that of a particle concentration at some time is proportional to the time.

Accordingly, when the carrying time of fine particles is long, the effects of aggregations of fine particles cannot be eliminated. In order to decrease the effects of such aggregations, it is considered to shorten the carrying time of fine particles, or to decrease the initial particle concentration of fine particles. In order to shorten the carrying time of fine particles, it is considered to increase the gas velocities of carrier gas and sheath gas, or to shorten a distance between second aerosol carrying pipe 114 and minute-ampere meter 124.

In addition, the initial particle concentration of fine particles also depends on the generation method of fine particles. Accordingly, it is effective to miniaturize fine-particle classification apparatus 801, further to use a small-sized pump as a vacuum pump composing sheath gas differential-exhaustion system 126, and to shorten the distance between second aerosol carrying pipe 114 and minute-ampere meter 124.

FIG. 9 illustrates the time dependency of the particle concentration of fine particles floating with the initial particle diameter of 10 nm.

As can been seen from FIG. 9, when the initial particle concentration of fine particles with the initial diameter of 10 nm is $10^{12}$ particles/m$^3$, the time required by that the initial particle concentration becomes half is more than about 1.0 sec. In other words, when the time required by that the fine particles are carried to minute-ampere meter 124 from second aerosol carrying pipe 114 is within 1.0 sec, it is possible to suppress that the initial particle concentration of fine particles is decreased to the half thereof. In this case, it is possible to suppress the effects of aggregations of fine particles considerably.

Specifically, the carrying path from second aerosol carrying pipe 114 to minute-ampere meter 124 is composed of pipes with a diameter of 0.5 inch. The carrying distance between second aerosol carrying pipe 114 and minute-ampere meter 124 is set to 50 cm. The flow rate of carrier gas is 1SLM (1/min at 0° C. and 1 atmospheric pressure). Under these conditions, the carrying velocity for fine particles when the operation pressure of fine-particle classification apparatus 801 is about 50 Torr (in other words, the pressure inside carrier gas pipe is about 50 Torr) is about 2.2 m/sec. Therefore, the time required by the carry of the fine particles is estimated to be about 0.23 sec. It is thus achieved to obtain fine-particle classification apparatus 801 in which the time required by that the particles are carried from second aerosol carrying pipe 114 to minute-ampere meter 124 is within 1.0 sec. In such an device, it is possible to classify and detect fine particles with the diameter of 10 nm when the operation pressure in fine-particle classification apparatus 801 is in a range of 20 to 50 Torr.

As described above, by miniaturizing fine-particle classification apparatus 801, it is possible to provide a fine-particle classification apparatus which is easy to carry and enables the easy attachment thereof to any kind of aerosol generation apparatus.

As described above, in fine-particle classification apparatus 801 according to the second embodiment, flat portions A802 and B803 are in the form of rectangles, so that fine-particle classification apparatus 801 has classification region 806 in the form of a rectangle. As a result, it is made possible to classify fine particles efficiently.

Further, the cross-section area of classification region 806 is made equal to or larger than that of the pipe at the upper stream portion than sheath gas introduction inlet 813. Thus, the cross-section area of classification region 806 can be decreased to a value equal to that of the cross-section area of the pipe at the upper stream portion than sheath gas introduction inlet 813. As a result, it is possible to decrease the sheath gas capacity inside fine-particle classification apparatus 801. Further, it is possible to decrease the effective exhaustion rate and exhaustion capacity of a vacuum pump placed at a downstream portion than sheath gas exhaustion outlet 815. Furthermore, in the case where the cross-section area of classification region 806 is made equal to that of the pipe at the upper stream portion than sheath gas introduction inlet 813, it is possible to prevent rapid changes of conductance in front and rear portions of sheath gas introduction inlet 813. Thus, it is possible to suppress stagnation from being generated in the flow of sheath gas.

In addition, in the second embodiment, the form of the cross section of the sheath gas pipe at the upper stream portion than sheath gas introduction inlet 813 is continuously changed to the form of the cross section of classification region 806. It is thereby possible to prevent the rapid changes of the form of sheath gas path in the front and rear potions of sheath gas introduction inlet 813. As a result, it is possible to suppress stagnation and disorder of the sheath gas flow, and to keep the laminar flow thereof.

Further, in the second embodiment, the four corners of the cross section of classification region 806 are cut to be circles, thereby facilitating that the sheath gas being flown from the pipe in the form of a cylinder at the upper stream portion than sheath gas introduction inlet 813 keeps the laminar flow inside fine-particle classification apparatus 801.

In addition, according to the second embodiment, it is possible to carry the fine particles, which are generated at a pressure less than the atmospheric pressure and then ionized in ionization chamber 117, to fine-particle classification apparatus 801 with the differential exhaustion to classify.

In addition, in the second embodiment, the operation pressure inside classification region 806 is less than 50 Torr. It is thereby possible to carry the fine particles, which are generated at a pressure less than 50 Torr and then ionized in ionization chamber 117, to fine-particle classification apparatus 801 with the differential exhaustion to classify.

Further, in the second embodiment, the time required by the fine particles being carried from second aerosol carrying pipe 114 to minute-ampere meter 124 is within 1.0 second. By thus shorting the carrying time spent by the fine particles being introduced and then detected, it is possible to reduce the effects of the aggregations of fine particles in the carrying process.

The present invention is not limited to the above described embodiments, and various variations and modifications may be possible without departing from the scope of the present invention.

This application is based on the Japanese Patent Application No.HEI10-314297 filed on Nov. 5, 1998, entire content of which is expressly incorporated by reference herein.

What is claimed is:

1. A low pressure functional material production apparatus comprising:

an aerosol generation section which generates an aerosol containing fine particles by irradiating a laser beam on a first target material in a low pressure background gas;

an introduction section which introduces the aerosol generated in the aerosol generation section to a fine particle classification section;

the fine particle classification section comprising an apparatus capable of classifying the fine particles based on electrical mobility, which classifies the fine particles, in a sheath gas, from the aerosol, in a low pressure background gas; and a deposition section which receives fine particles classified in the fine particle classification section and receives species generated by irradiating a laser beam on a second target material, and deposits the classified fine particles and the species on the substrate, in a low pressure background gas.

2. The apparatus of claim 1, wherein the introduction section introduces the aerosol to the classification system using a carrier gas with a velocity sufficient to introduce the aerosol into the classification section using a static pressure differential.

3. The apparatus of claim 1, wherein the deposition section receives the species at substantially the same time as collecting the classified fine particles on the substrate and disperses the classified particles in the species.

4. The apparatus of claim 1, wherein the deposition section receives the species at substantially the same time after collecting the classified fine particles on the substrate and dispersing the classified particles in the species.

5. The apparatus of claim 1, wherein the deposition section further comprises a target exchange mechanism which exchanges the second target material for a third transparent electrode target material, irradiates the third material with a laser beam to generate species which are deposited on the classified fine particles and species of the second target material, so as to form a transparent electrode.

6. The apparatus of claim 1, wherein the deposition section is configured to deposit the classified fine particles and the species composed of the second target material from a direction normal to the substrate.

7. The apparatus of claim 1, wherein the classification section comprises a charging section, which electrically charges the fine particles using a radioactive isotope.

8. The apparatus of claim 1, wherein the classification section comprises a charging section which electrically charges the fine particles using a vacuum ultraviolet light source.

9. The apparatus of claim 1, wherein the aerosol generation section charges the fine particles generated with the laser beam as a pulse laser in an ablation plume caused by a pulse laser beam.

10. The apparatus of claim 1, wherein the deposition section measures an electron transfer carried out as classified charged fine particles are deposited using an electric current.

11. The apparatus of claim 5, wherein the deposition section carries out deposition of both or either of the second and third target materials by sputtering.

12. The apparatus of claim 1, wherein the operating pressure in the classification section is less than 50 Torr.

13. The apparatus of claim 1, wherein the time required to transfer the fine particles from the introduction section to the deposition section is within 1 second.

14. The apparatus of claim 1, wherein the density of the carrier gas is greater than the density of the low pressure background gas inside the aerosol generation section.

15. The apparatus of claim 1, wherein a density of the sheath gas is greater than the density of the low pressure background gas inside the aerosol generation section.

16. The apparatus of claim 1, wherein the carrier gas is in a viscous flow state.

* * * * *